United States Patent
Jingu

(10) Patent No.: US 9,791,380 B2
(45) Date of Patent: Oct. 17, 2017

(54) INSPECTION DEVICE AND IMAGE CAPTURE ELEMENT

(71) Applicant: HITACHI HIGH-TECHNOLOGIES CORPORATION, Tokyo (JP)

(72) Inventor: Takahiro Jingu, Tokyo (JP)

(73) Assignee: HITACTHI HIGH-TECHNOLOGIES CORPORATION, Tokyo (JP)

( * ) Notice: Subject to any disclaimer, the term of this patent is extended or adjusted under 35 U.S.C. 154(b) by 414 days.

(21) Appl. No.: 14/391,338

(22) PCT Filed: Apr. 8, 2013

(86) PCT No.: PCT/JP2013/060600
§ 371 (c)(1),
(2) Date: Oct. 8, 2014

(87) PCT Pub. No.: WO2013/154067
PCT Pub. Date: Oct. 17, 2013

(65) Prior Publication Data
US 2015/0109434 A1    Apr. 23, 2015

(30) Foreign Application Priority Data
Apr. 9, 2012   (JP) ................... 2012-088733

(51) Int. Cl.
*G01N 21/95* (2006.01)
*G01N 21/88* (2006.01)
*G01N 21/956* (2006.01)

(52) U.S. Cl.
CPC ..... *G01N 21/9501* (2013.01); *G01N 21/8803* (2013.01); *G01N 21/8806* (2013.01); *G01N 21/8851* (2013.01); *G01N 21/956* (2013.01)

(58) Field of Classification Search
CPC .................................................. G01N 21/9501
(Continued)

(56) References Cited

U.S. PATENT DOCUMENTS 4,740,079 A     4/1988 Koizumi et al.
6,184,929 B1 *  2/2001 Noda ....................... H04N 1/03
                                                         348/275

(Continued)

FOREIGN PATENT DOCUMENTS

JP      61-104242 A    5/1986
JP      61-104243 A    5/1986
(Continued)

OTHER PUBLICATIONS

International Search Report issued in International Application Na PCT/JP2013/060600 dated Jun. 11, 2013, with English Translation.

*Primary Examiner* — Mohammed Rahaman
*Assistant Examiner* — Asmamaw G Tarko
(74) *Attorney, Agent, or Firm* — McDermott Will & Emery LLP

(57) ABSTRACT

An imaging device includes multiple sensor pixels that are arranged in a predetermined direction, each sensor pixel having multiple sensor pixel borders defining an outer edge part of the sensor pixel, among which at least one of a pair of sensor pixel borders that are opposed in the arrangement direction is oblique to a passage direction of a defect image that is vertical to the predetermined direction. This can provide an inspection tool enabling high sensitivity inspection and/or having improved detection reproducibility of a defect.

20 Claims, 12 Drawing Sheets

(58) Field of Classification Search
USPC .......................................................... 348/126
See application file for complete search history.

(56) References Cited

U.S. PATENT DOCUMENTS

| | | | |
|---|---|---|---|
| 7,009,163 B2* | 3/2006 | Katzir | G01N 21/8851 250/208.1 |
| 8,208,356 B2* | 6/2012 | Ishihara | G11B 20/18 356/237.2 |
| 2011/0158073 A1 | 6/2011 | Ishihara et al. | |
| 2013/0003052 A1* | 1/2013 | Nakao | G01N 21/47 356/237.5 |

FOREIGN PATENT DOCUMENTS

| | | |
|---|---|---|
| JP | 61-104244 A | 5/1986 |
| JP | 61-104658 A | 5/1986 |
| JP | 61-117433 A | 6/1986 |
| JP | 07-270144 A | 10/1995 |
| JP | 9-266517 A | 10/1997 |
| JP | 2005-520123 A | 7/2005 |
| JP | 2007-333662 A | 12/2007 |
| JP | 2009-042113 A | 2/2009 |
| JP | 2009-244256 A | 10/2009 |
| JP | 2011-137721 A | 7/2011 |
| JP | 2011-158260 A | 8/2011 |
| WO | 03/001189 A1 | 1/2003 |

* cited by examiner

FIG. 8
(A)
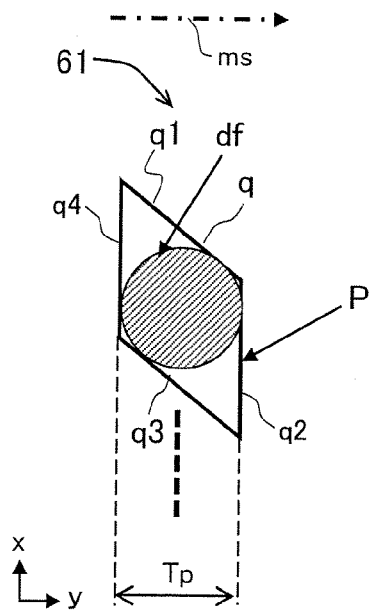
(B)
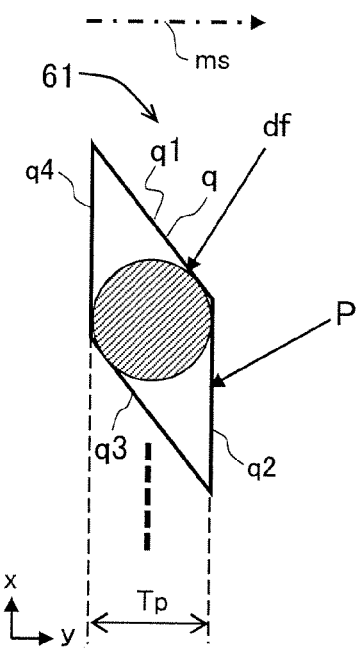
(C)
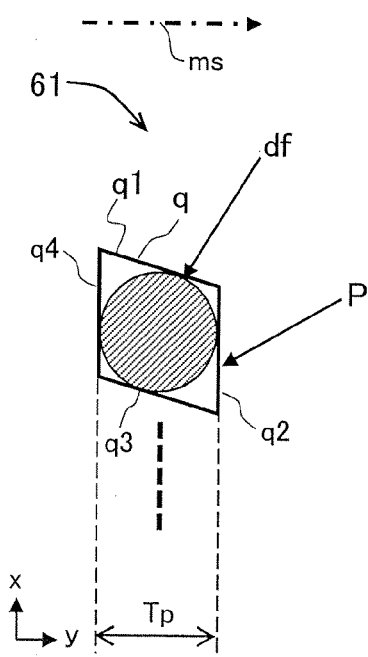
(D)
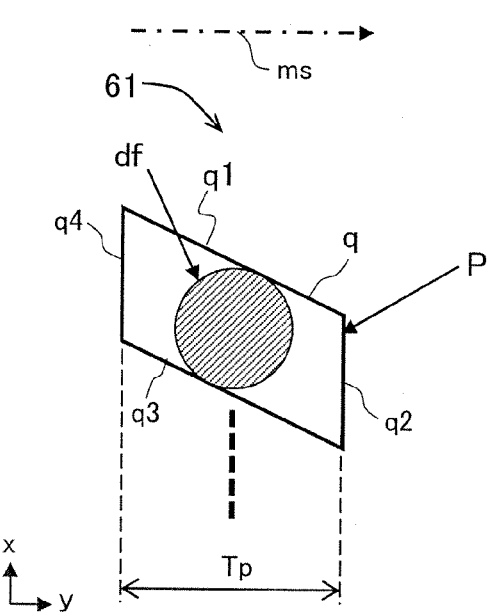

FIG. 9
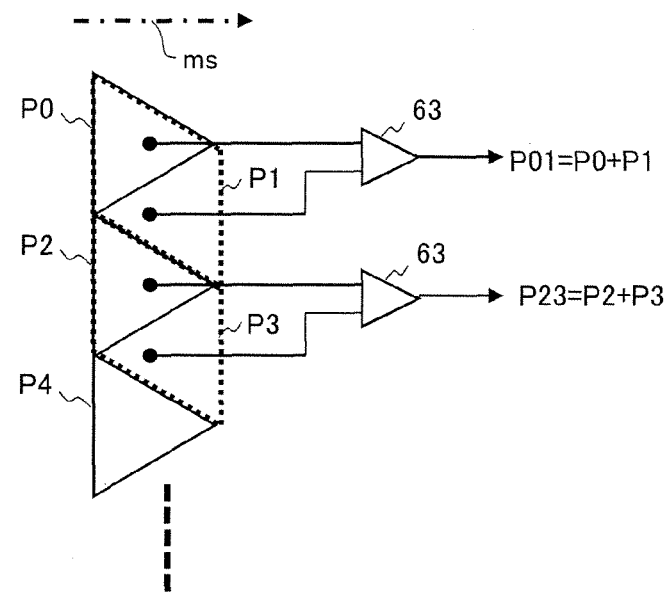
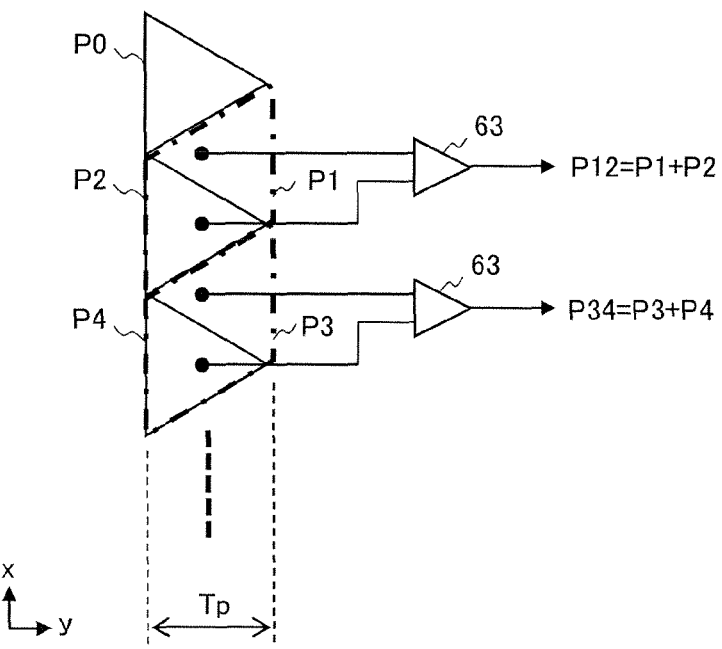

FIG. 10
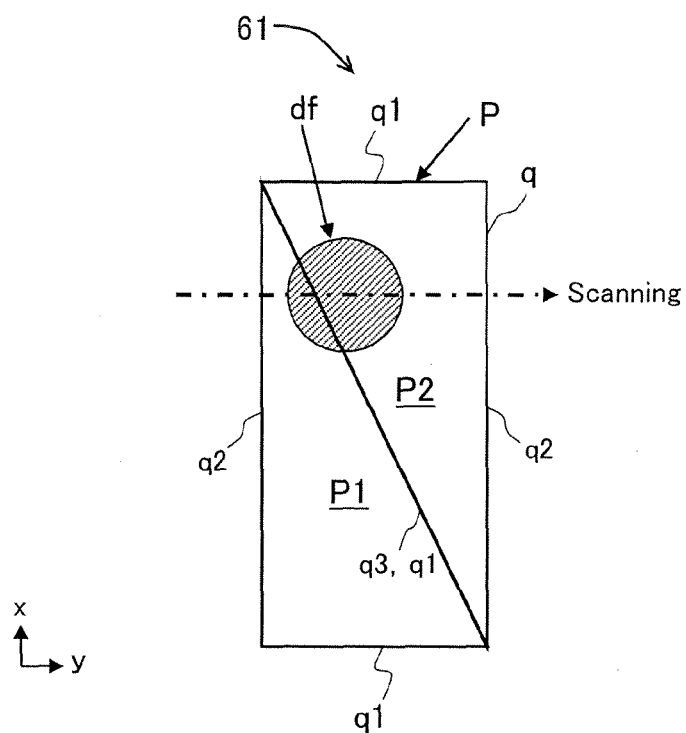
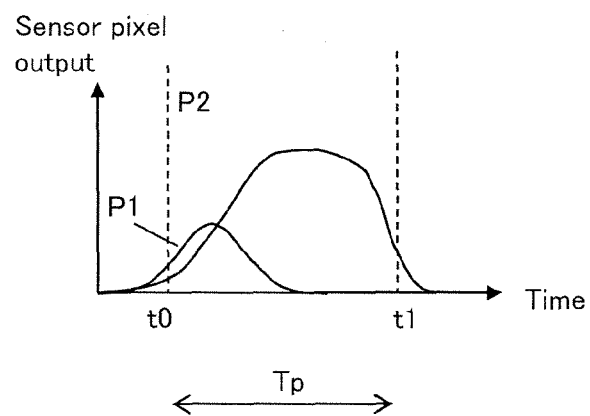

FIG. 11

Comparative example 1

| | Examined model | S/N ratio |
|---|---|---|
| Case 1: Sensor pixel center and defect image center agree | | S/N ratio: 1 (reference value) Background light (noise component is uniform) |
| Case 2: Sensor pixel border of sensor pixel and defect image center agree | | S/N ratio: One pixel: 1/2 Average processing of neighboring pixels performed: $1/(\sqrt{2})$ (relative value with case 1) |
| Case 3: State between cases 1 and 2 | | S/N ratio: 1/(determined with passage position) (relative value with case 1) |

FIG. 12
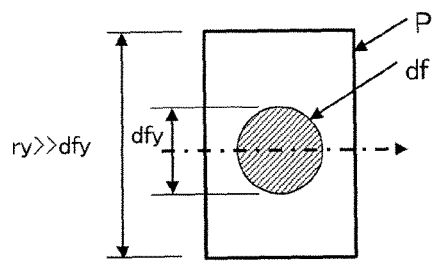
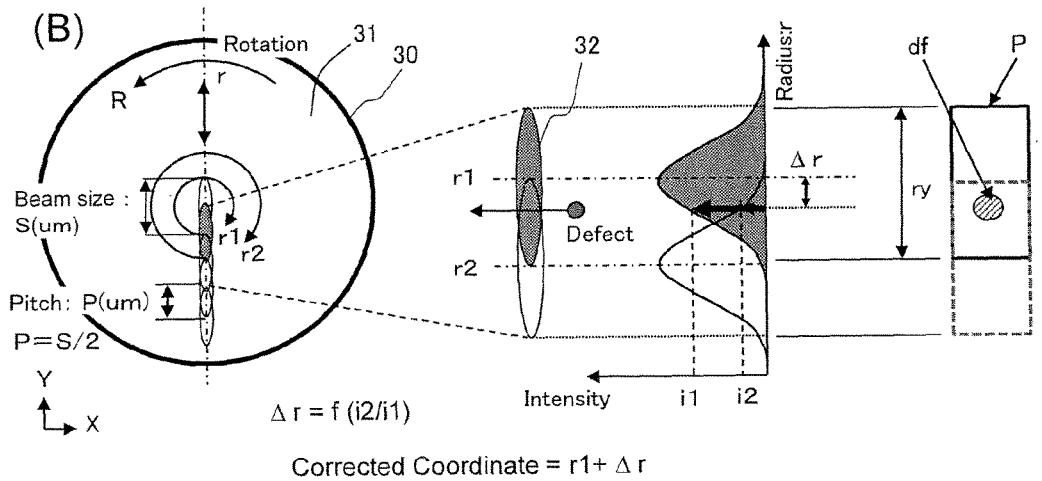
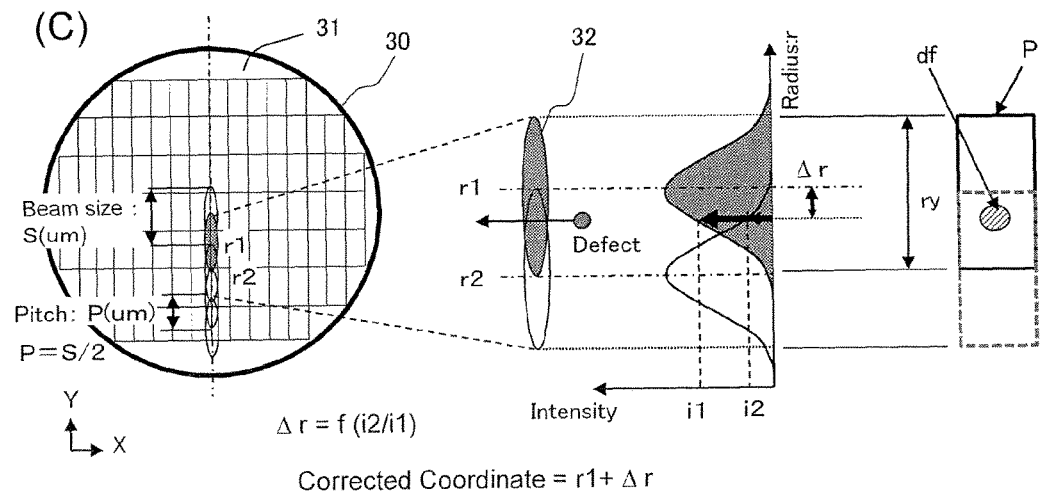

INSPECTION DEVICE AND IMAGE CAPTURE ELEMENT

RELATED APPLICATIONS

This application is a national phase of International Application No. PCT/JP2013/060600, filed on Apr. 8, 2013, which in turn claims the benefit of Japanese Application No. 2012-088733, filed on Apr. 9, 2012, the disclosures of which Applications are incorporated by reference herein.

TECHNICAL FIELD

The present invention relates to inspection tools configured to inspect a defect on a substrate such as a semiconductor wafer, and relates to imaging devices used for such an inspection tool.

BACKGROUND ART

During semiconductor manufacturing process, defects such as particles and scratches on the surface of a semiconductor wafer may lead to malfunctions such as poor insulation or a short of wiring formed on the wafer surface. Along with finer design rules for circuit pattern, smaller defects may cause poor insulation of a capacitor as a patterned element and failures in a gate oxidation film or the like. Defects on a semiconductor wafer prior to the formation of a circuit pattern, i.e., on the surface of a bare wafer similarly affect electrical characteristics of the circuit pattern formed later. That is, it is important for semiconductor manufacturing process to detect a defect on a semiconductor wafer as a substrate for each step and to feed back such a defect to the related manufacturing steps.

Such a defect on a substrate such as a semiconductor wafer is detected by an inspection tool. An example of such a type of inspection tools includes an optical inspection tool configured to irradiate the substrate surface with light (inspection light) and detect scattered light generated from the irradiated substrate surface, and detect a defect on the substrate based on a result of the detection.

This type of inspection tool used as a defect inspection tool to inspect a defect on a semiconductor wafer, for example, is roughly classified according to the usage into a surface inspection tool to inspect a defect on a bare wafer such as a mirror-surface wafer having a surface subjected to mirror finish by polishing process, and a pattern inspection tool to inspect a defect on a patterned wafer with a circuit pattern formed thereon.

For both of these surface inspection tool and pattern inspection tool, inspection tools are configured to detect scattered light generated from an illumination spot on a substrate that is irradiated with light by an optical detector, thus obtaining a detection signal of the scattered light corresponding to the amount of detection. The optical detector used in such a configuration is an imaging device having multiple sensor pixels. They may be configured to move and/or revolve a substrate as an inspection sample, thus scanning the illumination spot on the substrate irradiated with the light.

Such a type of inspection tools and imaging devices as conventional techniques are described in Patent Literatures 1 to 4.

CITATION LIST

Patent Literatures

Patent Literature 1: JP 2011-158260 A
Patent Literature 2: JP 2005-520123 A
Patent Literature 3: JP 2009-42113 A
Patent Literature 4: JP 2009-244256 A

SUMMARY OF INVENTION

Technical Problem

In such an inspection tool, it is desirable that each sensor pixel making up the imaging device of the optical detector have a sensor output, i.e., a pixel output of a higher S/N ratio indicating the ratio between a signal and noise. This is because a higher S/N ratio of each pixel output enables the detection of smaller defects on a substrate even when the output is small.

On the other hand, such an inspection tool preferably has the size of each sensor pixel of the imaging device of the optical detector, i.e., each pixel size that is equal to the optical resolution of a defect (defect image size). This is because, when the imaging device is a single sensor pixel, for example, i.e., when the pixel size is too large compared with the optical resolution of the defect, the position of the defect cannot be detected on the substrate unless overlap scanning of the illumination spot is performed while setting the illuminance distribution as the Gaussian distribution, meaning an increase in inspection time even with the S/N ratio of the pixel outputs that is a high value enabling the detection of a small defect.

In this way, an inspection tool having each pixel size of the imaging device of the optical detector that is equal to the defect image size can minimize the data processing amount in the system configuration, and can maximize the S/N ratio of the detected image of the optical resolution on the substrate between the case of detecting a defect image and the case of not detecting a defect image.

When the pixel size of the imaging device of the optical detector and the optical resolution of the defect (defect image size) are equivalent, however, the inspection tool does not directly move the illumination spot as the inspection part on the substrate, but moves and/or revolves the substrate as the inspection sample for relative movement on the substrate and for scanning. As the substrate is moved and/or revolved, the passage position of the defect image with reference to the sensor pixel on the imaging device may change in the vertical direction of the scanning direction. Then, the pixel output also changes, and the S/N ratio of the detected image of the defect also changes. For instance, when the center of the defect image does not agree with the center part of the sensor pixel of the imaging device, and a part of the defect image only passes through this sensor pixels while the center of the defect image agrees with the border part of this sensor pixel and the adjacent sensor pixel, the S/N ratio of the pixel output of this sensor pixel decreases to ½.

In such a case, the pixel outputs of the mutually adjacent sensor pixels may be averaged for adjacent pixel averaging processing to find the pixel output, whereby the S/N ratio of the pixel output of each sensor pixel can be improved to $1/(\sqrt{2})$. However, this processing decreases the optical resolution of the defect to half, and increases the resolved defect size that is the double of the actual size.

In this way, when the pixel size of the imaging device of the optical detector is equivalent to the defect image size, if a pixel dividing phenomenon is generated so that the passage position of the defect image on the sensor pixel of the imaging device is displaced in the vertical direction of the scanning direction, the defect detection sensitivity of the imaging device and accordingly of the inspection tool is degraded, which becomes a factor of degrading the detection reproducibility of the detected image of a defect. Such an image splitting phenomenon is not desired for the inspection, and is a big problem for the performance of the inspection tool. Conventional techniques, however, do not consider this respect sufficiently.

Solution to Problem

An inspection tool of the present invention is configured to irradiate a surface of a substrate with inspection light, detect scattered light generated from an illumination spot on the substrate surface that is irradiated with the inspection light by an imaging device, and detect a defect on the substrate based on an output from the imaging device. The imaging device includes multiple sensor pixels that are arranged in a direction vertical to a main scanning direction of the illumination spot with the inspection light on the substrate, each sensor pixel having multiple sensor pixel borders defining an outer edge part of the sensor pixel, among which at least one of a pair of sensor pixel borders that are opposed in the direction vertical to the main scanning direction is oblique to the main scanning direction that is a passage direction of a defect image.

An imaging device of the present invention includes multiple sensor pixels that are arranged in a predetermined direction to detect scattered light generated from an illumination spot on a substrate surface that is irradiated with the inspection light. Each sensor pixel has multiple sensor pixel borders defining an outer edge part of the sensor pixel, among which at least one of a pair of sensor pixel borders that are opposed in an arrangement direction is oblique to a passage direction of a defect image that is vertical to the predetermined direction.

This application claims the benefit of priority to JP Patent Application No. 2012-088733 based thereon, the specification and/or the drawings of which are herein incorporated by reference.

Advantageous Effects of Invention

The present invention can exert at least one of the following advantageous effects of:
(1) enabling an inspection with high sensitivity; and
(2) improving the detection reproducibility of a defect.
Problems, configurations, and advantageous effects other than those described above will be made clear by the following description of embodiments.

BRIEF DESCRIPTION OF DRAWINGS

FIG. 8 illustrates the configuration of an imaging device, which is used for a defect inspection tool according to Embodiment 4 of the present invention.

FIG. 9 describes one embodiment to reduce the scale of signal processing by a defect inspection tool according to Embodiment 5 of the present invention.

FIG. 10 describes a defect inspection tool including an imaging device of single pixel of a size that is larger in size of the optical resolution (defect size) that is Embodiment 6 of the present invention.

FIG. 11 illustrates Comparative Example 1.

FIG. 12 illustrates Comparative Example 2 and Comparative Example 3.

DESCRIPTION OF EMBODIMENTS

Figure 1:
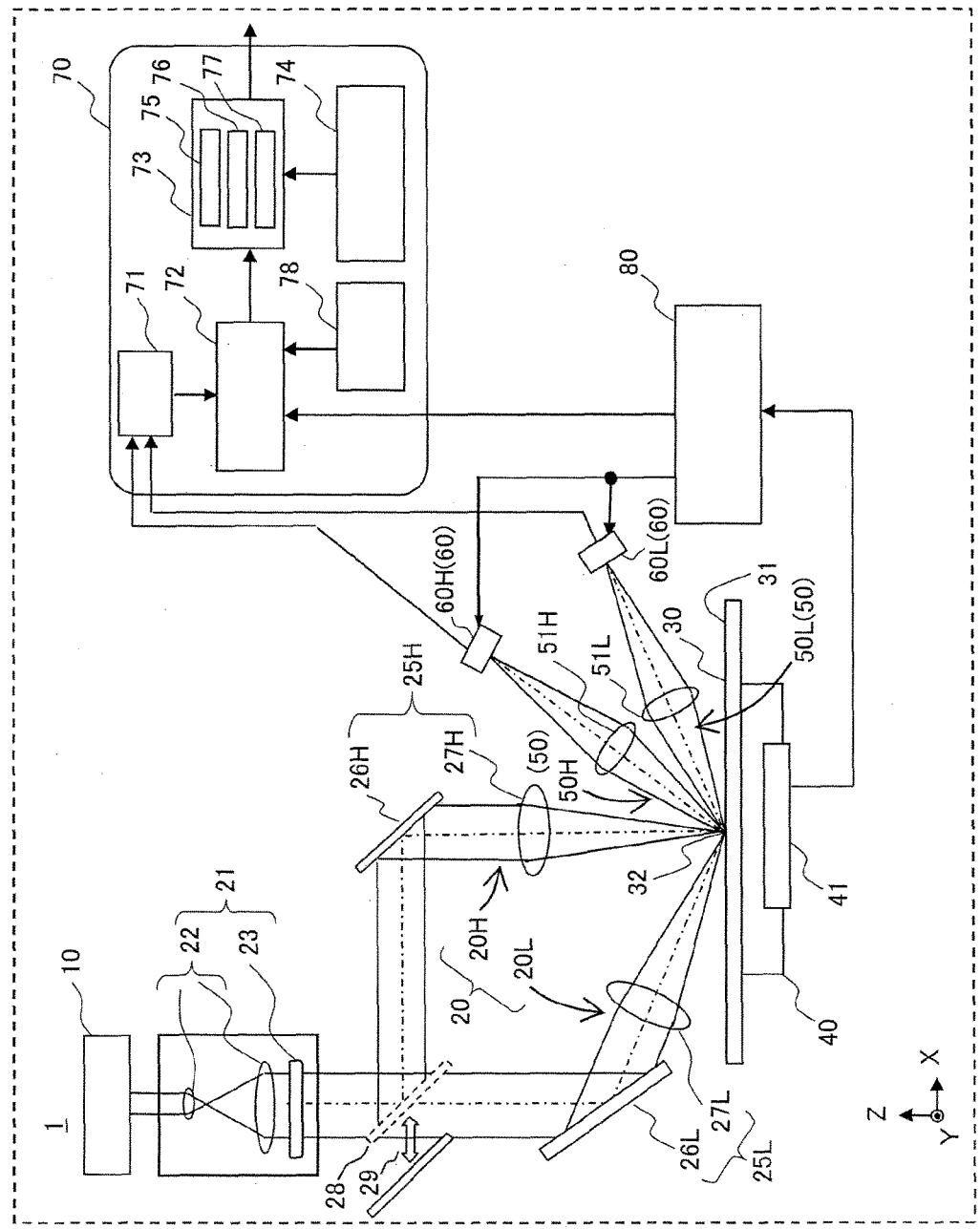
FIG. 1 schematically illustrates a defect inspection tool according to Embodiment 1 of the present invention.

An inspection tool and an image device according to the present invention can be used for inspections of a flat-panel shaped inspection sample such as a semiconductor wafer, a semiconductor mask, an array substrate of a liquid crystal panel, and a sapphire substrate and a ceramic substrate used for a sensor or a LED.

Referring to the drawings, the following describes embodiments of an inspection tool and an imaging device according to the present invention, by way of examples of a defect inspection tool to inspect a defect on a semiconductor wafer, and an imaging device used therefor.

Embodiment 1

FIG. 1 schematically illustrates a defect inspection tool to inspect a defect such as a particle or a scratch on the surface of a semiconductor wafer according to Embodiment 1 of the present invention.

As illustrated in FIG. 1, a defect inspection tool 1 of the present embodiment includes a light source 10, illumination optics 20 (20L, 20H), a stage mechanism 40, imaging optics 50 (50L, 50H), an optical detector 60 (60L, 60H) and a detection signal processor 70 and a control signal generator 80.

The light source 10 generates light (inspection light) to inspect a defect such as an extremely small particle on a semiconductor wafer 30. The light source 10 may include a laser light source that emits UV (Ultraviolet) light or DUV (Deep Ultraviolet) light, enabling intensive scattered light to be acquired from such an extremely small defect. The laser light source, for example, may emit a laser beam of 355 nm in wavelength $\lambda$.

The illumination optics 20 (20L, 20H) guide illumination light from the light source 10 on the semiconductor wafer 30 for irradiation. The illumination optics 20 include illumination shaping optics 21 and irradiation optics 25 (25L, 25H).

The illumination light from the light source 10 is adjusted to have a desired size in beam diameter by a beam expander 22 of the illumination shaping optics 21, and is converted into an illumination beam in a desired polarization state by a polarizing device 23. The illumination beam is linear polarization having an oscillation vector of the illumination light that oscillates in a plane including the normal line of a wafer surface 31 of the semiconductor wafer 30 held at the stage mechanism 40 and the travelling direction of the illumination light.

The illustrated example is configured so that the illumination beam subjected to shaping by the illumination shaping optics 21 is supplied to any one of the irradiation optics 25L and 25H by a movable mirror 28 arranged movable forward and backward to the illumination optical path on the output side of the illumination shaping optics 21 in response to the action of a switching mechanism 29. The irradiation optics 25L irradiate the illumination beam shaped by the illumination shaping optics 21 so as to be at a low angle (oblique) to the wafer surface 31 of the semiconductor wafer 30 and the irradiation optics 25H irradiate such illumination beam so as to be normal to the wafer surface 31 of the semiconductor wafer 30. This allows the selection of the illumination optical path to the wafer surface 31 between a low angle (oblique) and normal in response to the action of the switching mechanism 29 that is installed to the movable mirror 28.

The illumination beam is obliquely incident with a predetermined illumination elevation angle, e.g., with a Brewster angle to crystalline silicone (Si) on the wafer surface 31 of the semiconductor wafer 30 mounted on the stage mechanism 40 via reflective mirrors 26L, 26H and collecting lenses 27L and 27H having a cone curved surface of the irradiation optics 25L and 25H. A part of the wafer surface 31 of the semiconductor wafer 30 that is irradiated with the illumination beam corresponds to an illumination spot 32. In this case, the illumination spot 32 on the wafer surface 31 has illuminance distribution along the direction vertical to the scanning direction that is not in a Gaussian shape but in a flat shape.

The stage mechanism 40 includes a stage (not illustrated), on which the semiconductor wafer 30 as an inspection sample is to be mounted during inspection, and a stage move mechanism (not illustrated) to move this stage. During the inspection, the stage mechanism 40 is controlled in its driving by a stage controller not illustrated based on a type of the inspection sample and an inspection method set beforehand.

The stage move mechanism includes a stage horizontal move mechanism to move the stage in a straight line one dimensionally in a plane along the sample mounting face or two dimensionally, and includes a stage revolve mechanism to revolve the stage in a face along the sample mounting face and a stage vertical move mechanism to move and displace the stage in the direction vertical to the sample mounting face as needed.

For instance, when the defect inspection tool 1 is used as a surface inspection tool to inspect a defect on a bear wafer without any pattern formed thereon, the stage mechanism 40 is configured so that the stage revolve mechanism can revolve the stage with the semiconductor wafer 30 mounted thereon at a constant angular velocity during the inspection, and the stage horizontal move mechanism can move the stage in a straight line with a predetermined pitch along the radial direction of the semiconductor wafer 30 that revolves together while synchronizing it with the revolving of the stage by the stage revolve mechanism. This allows the illumination spot 32 corresponding to the irradiation position on the semiconductor wafer 30 with the illumination beam by the irradiation optics 25 (25L, 25H) to be scanned in a concentric or a spiral-shaped manner on the wafer surface 31, whereby an image of the entire wafer surface or the scanning region part can be captured by the optical detector 60 (60L, 60H) via the imaging optics 50 (50L, 50H).

Such scanning of the illumination spot 32 with the illumination beam on the semiconductor wafer 30 includes a relative movement along the wafer revolving direction (R direction) of the illumination spot 32 on the semiconductor wafer 30 that is revolved by the action of the stage revolve mechanisms, which is called primary scanning of the illumination spot 32, and a relatively straight movement in the wafer radius direction (r direction) of the illumination spot 32 on the semiconductor wafer 30 that is moved in a straight line along the wafer radius direction (r direction) by the action of the stage horizontal move mechanism, which is called secondary scanning of the illumination spot 32.

Meanwhile, when the defect inspection tool 1 is used as a pattern inspection tool to inspect a defect on a patterned wafer with a pattern already formed thereon, the stage mechanism 40 is configured so that the stage horizontal move mechanism moves the stage with the semiconductor wafer 30 mounted thereon in a straight line along one chip arrangement direction (X direction) of multiple chips arranged like a grid on the wafer surface 31 during the inspection, and moves the stage along the other chip arrangement direction (Y direction) as well while synchronizing it with the straight movement of the stage in the one chip arrangement direction (X direction). This allows the illumination spot 32 corresponding to the irradiation position on the semiconductor wafer 30 with the illumination beam by the irradiation optics 25L, 25H to be scanned two dimensionally along these arrangement directions (X-Y direction) of the multiple chips on the wafer surface 31, whereby an image of the entire wafer surface or the scanning region part of the semiconductor wafer 30 can be captured by the optical detector 60L, 60H via the imaging optics 50L, 50H. Such scanning of the illumination spot 32 with the illumination beam on the semiconductor wafer 30 includes a relative movement along the X direction of the illumination spot 32 on the semiconductor wafer 30 that is moved in a straight line along the one chip arrangement direction (X direction) by the action of the stage horizontal movement mechanisms, which is called primary scanning of the illumination spot 32, and a relative movement along the Y direction of the illumination spot 32 on the semiconductor wafer 30 that is moved in a straight line along the other chip arrangement direction (Y direction) by the action of the stage horizontal move mechanism, which is called secondary scanning of the illumination spot 32.

Aside from the above scanning of the illumination spot 32 on the semiconductor wafer 30, the stage mechanism 40 may be configured so that the stage vertical move mechanism adjusts the height position of the wafer surface 31 of the semiconductor wafer 30 with reference to the irradiation optics 25L, 25H and the imaging optics 50L, 50H by displacing the stage in the height direction (Z direction) in accordance with the thickness or the like of the semiconductor wafer 30 as an inspection sample to be mounted on the stage.

Such a stage mechanism 40 is provided with a position detection encoder 41 to detect the amount of movement of the stage or the movement position of the stage that is moved in a straight line by the action of the stage horizontal move mechanism and the stage vertical move mechanism or to detect the amount of revolving of the stage or the revolving position of the stage that is revolved by the action of the stage revolve mechanism. The position detection encoder 41 sends out these detection results to the control signal generator 80 via an encoder pulse.

In the illustrated example, the imaging optics 50 and the optical detector 60 include multiple detector units 50L and 60L and 50H and 60H having different azimuth angles to the illumination spot 32 and different detection elevation angles to the wafer surface 31.

The imaging optics 50L and 50H have detection lenses 51L and 51H, polarizing devices (not illustrated) and imaging lenses (not illustrated). The imaging optics 50L, 50H are layouted so as to have different detection elevation angles or detection azimuth angles to the wafer surface 31 of the semiconductor wafer 30 held at the stage mechanism 40 or to have both of such angles that are different, enabling the detection lens 51L, and 51H to effectively capture the scattered light from a small particle, which follows the Rayleigh scattering.

The detection lenses 51L and 51H have an aperture (NA: numerical aperture) that is set at a predetermined value suitable for the optical resolution of a desired detectable defect (defect image size). The polarizing device reduces scattered light generated from microscopic asperities on the wafer surface 31 (denoted as "roughness scattered light") to enable the detection of more minute defects.

The imaging optics 50L and 50H include the detection lenses 51L and 51H as objective lenses to collect the scattered light from the wafer surface part at the illumination spot 32 on the semiconductor wafer 30 that is irradiated with the illumination beam, and form an image of the wafer surface part at the illumination spot on the detection surface of the optical detectors 60L and 60H via the polarizing device and the imaging lenses.

The optical detectors 60L and 60H detect the scattered light collected by the detection lenses 51L and 51H of the imaging optics 50L and 50H, and convert it into an electrical signal corresponding to the amount of detection and output it as a scattered light detection signal. The optical detectors 60L and 60H includes an imaging device having a detection surface made up of multiple sensor pixels (photoelectric conversion sensor) that output an electrical signal (light-amount signal) of the magnitude corresponding to the amount of light received. Exemplary imaging devices include a CCD (Charge Coupled Device imager) and a TDI (Time Delayed Integration), and the sensor pixels thereof used may be a PD (Photo Diode), an APD (Avalanche Photo Diode) and the like.

As the pixel size of the sensor pixels of the imaging device decreases, the throughput thereof deteriorates, but a defect such a smaller particle can be detected. Then, the following describes the configuration of the imaging device that is used for the optical detectors 60L and 60H of the defect inspection tool 1 of the present embodiment in details, with reference to FIG. 2.

Figure 2:
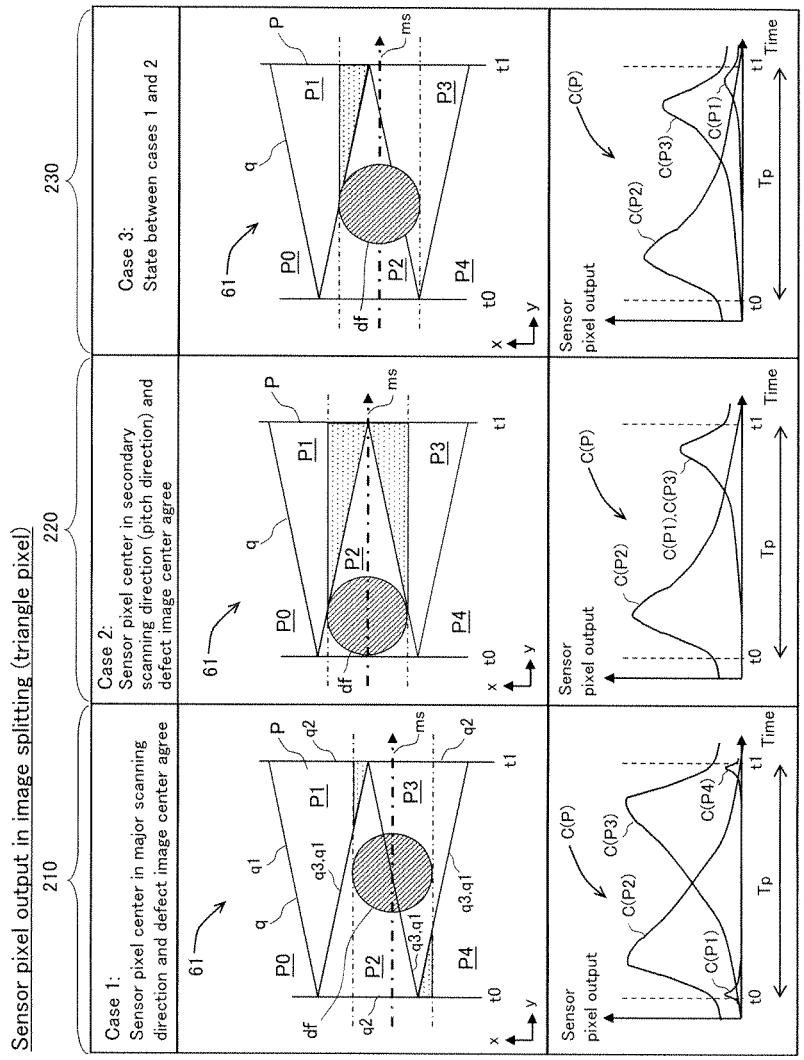
FIG. 2 shows the configuration of an imaging device of an optical detector that is used for the defect inspection tool of FIG. 1 and describes how to detect a defect by the defect inspection tool.

FIG. 2 shows the configuration of an imaging device of an optical detector that is used for the defect inspection tool of FIG. 1 and describes how to detect a defect by the defect inspection tool.

In FIGS. 1 and 2, the imaging device 61 of each of the optical detectors 60L and 60H includes at least two multiple sensor pixels P (in the illustrated example, P0, P1, P2, P3, P4 . . . ) arranged in the direction vertical to the primary scanning direction of the illumination spot 32 on the wafer surface 31, i.e., in the secondary scanning direction of the illumination spot 32 on the wafer surface 31. In the illustrated example, each sensor pixel P has the size that is equal to the optical resolution of a defect (defect image size) so as to increase the S/N ratio of the pixel output.

In FIG. 2, the arrow ms corresponds to the passage direction of a defect image df of a defect for the sensor pixel P on the semiconductor wafer 30 that is imaged by the imaging optics 50L and 50H, corresponding to the primary scanning of the illumination spot 32. In the x-y coordinates, the x axis corresponds to the passage direction ms of the defect image df for the sensor pixel P, corresponding to the primary scanning direction of the illumination spot 32. On the other hand, the y axis corresponds to the direction vertical to the passage direction ms, corresponding to the secondary scanning direction of the illumination spot 32.

In the illustrated example, each sensor pixel P has the size that is equal to the optical resolution of a defect (defect image size), which is greatly smaller than the overall size of the wafer surface of the semiconductor wafer 30. That is, irrespective of the defect inspection tool 1 being any one of a surface inspection tool and a pattern inspection tool, i.e., irrespective of a difference between the primary scanning direction of the illumination spot 32 being the wafer revolving direction (R direction) and being one chip arrangement direction (X direction) of the grid, the passage state of the defect image df to the sensor pixel P is substantially the same.

Each sensor pixel P has a configuration so that the outer shape of the detection surface of the sensor pixel P is defined with at least three sensor pixel borders q. Among at least three sensor pixel borders q of one sensor pixel P, at least one sensor pixel border q doubles as a sensor pixel border q of the neighboring sensor pixel P. In the illustrated example, each sensor pixel P has a triangle shape, and so a sensor pixel P1, for example, has sensor pixel borders q1, q2 and q3, among which the sensor pixel border q3 doubles as a sensor pixel border q1 of the neighboring sensor pixel P2.

Then, among at least three sensor pixel borders q of one sensor pixel P, at least one of a pair of sensor pixel borders q that are opposed in the arrangement direction of the sensor pixels P that is vertical to the passage direction ms of the defect image df to the sensor pixels P on the sensor pixels is inclined to the primary scanning direction (R direction or X direction) of the illumination spot 32.

Specifically in the illustrated example, each sensor pixel P0, P1, P2, P3 . . . of each imaging device 61 has an isosceles triangle defined with a bottom side that is parallel to the direction vertical to the passage direction ms of the defect image df to the sensor pixels P and a height that is parallel to the passage direction ms of the defect image df to the sensor pixels P. Such an isosceles triangle shape and the size of each pixel P is configured so that, when the center of the defect image df at the optical resolution passes through the center part of the bottom side of the sensor pixel P in the isosceles triangle shape along the height direction of the triangle, the defect image df temporally is inscribed in the sensor pixel borders q1 and q3 making up a single pair of oblique lines on the pixel face or in all of the sensor pixel borders q1, q2 and q3, and at the time of this inscription, the defect image df as a whole is overlapped on the pixel face of the sensor pixel P.

In the illustrated example, the imaging device 61 includes a plurality of such sensor pixels P1, P2, P3 . . . having an isosceles triangle shape that are arranged in the direction vertical to the passage direction ms of the defect image df for the sensor pixel P, corresponding to the second scanning direction of the illumination spot 32, while reversing the directions of adjacent sensor pixels P in their height direction.

As illustrated in FIG. 1, the optical detectors 60L and 60H are configured so that the pixel output of each sensor pixel P making up the imaging devices 61 of the optical detectors 60L and 60H is scanned and extracted at a predetermined sampling rate based on the driving signal (sensor pixel scanning signal) supplied from the control signal generator 80, and the pixel output (light-amount signal) of each sensor pixel P is sent out to the detection signal processor 70 as the scattered light detection signal. In this case, the sampling rate of the pixel output of the sensor pixel P that is given based on the driving signal (sensor pixel scanning signal) is greatly shorter than the passage time Tp required for the defect image df of the optical resolution (defect size) to pass over one sensor pixel P while synchronizing with the scanning (primary scanning) of the illumination spot 32, i.e., the sampling time of the defect image df. This allows the sensor pixel P to successively detect, as the pixel output, a change in the passage state of the defect image df passing over the sensor pixel P with reference to the pixel face.

The control signal generator 80 monitors the scanning position of the illumination spot 32 on the semiconductor wafer 30 that is mounted on the stage of the stage mechanism 40 based on the encoder pulse supplied from the position detection encoder 41 installed to the stage mechanism 40 that is controlled by the stage controller not illustrated, while supplying the driving signal to the optical detectors 60L and 60H, and sends out a sampling control signal to the detection signal processor 70 as well to control their actions.

As illustrated in FIG. 1, the detection signal processor 70 includes an A/D converter 71, a signal feature extraction unit 72, a defect information processing unit 73, and an operation basic data storage unit 74, and is configured to process a scattered light detection signal supplied from the optical detectors 60L and 60H to detect a defect on the semiconductor wafer 30.

The A/D converter 71 receives a scattered light detection signal including the pixel output of each sensor pixel P of the imaging device 61 that is sent out from each of the optical detectors 60L and 60H to A/D convert the same, and supplies it to the signal feature extraction unit 72.

The signal feature extraction unit 72 fetches the digitized scattered light detection signal that is successively supplied from the A/D converter 71, and divides the pixel output of each of the multiple sensor pixels P for each pixel P for storage. Meanwhile the signal feature extraction unit 72, in parallel with the storage of the pixel output for each sensor pixel P as stated above, extracts a set of the pixel outputs corresponding to the passage time Tp required for the defect image df of the optical resolution (defect size) over one sensor pixel P, i.e., the sampling time of the defect image df from the stored pixel outputs for each sensor pixel P based on the sampling control signal supplied from the control signal generator 80, and successively generates a signal feature C(P) of the pixel output for each pixel P. The signal feature extraction unit 72 performs, for each sensor pixel P, such generation of the signal feature C(P) of the pixel output for each sensor pixel P.

The signal feature extraction unit 72 successively supplies the thus generated signal feature C(P) of the pixel output for each sensor pixel P to the defect information processing unit 73.

Cases 1 and 3 illustrated in the fields 210 and 230 of FIG. 2 show that exemplary passage states of the defect image df when the defect image df of the optical resolution (defect size) passes without temporarily being inscribed in the sensor pixel borders q1 and q3 defining the single pair of oblique lines over the pixel face of the sensor pixel P, and show signal features C(P1) to C(P4) of the pixel outputs of the sensor pixels P1 to P4 generated by the signal feature extraction unit 72 during the passage. On the other hand, case 2 illustrated in the field 220 of FIG. 2 shows that an exemplary passage state of the defect image df when the defect image df passes while being temporarily inscribed in the sensor pixel borders q1 and q3 defining the single pair of oblique lines over the pixel face of the sensor pixel P and being inscribed in the sensor pixel border q3 as well to be temporally inscribed in all sensor pixel borders q1, q2 and q3, and show signal features C(P1) to C(P4) of the pixel outputs of the sensor pixels P1 to P4 generated by the signal feature extraction unit 72 during the passage. Between case 1 in the field of 210 and case 3 in the field of 230, while case 1 shows that the center of the defect image df passes through the center part in the length direction of the sensor pixel borders q inclined to the passage direction ms over the pixel face of the defect image df, case 3 shows that the center of the defect image df passes through off from the center in the length direction of the sensor pixel border q3 of the sensor pixel P2 that is inclined to the passage direction ms over the pixel face of the defect image df, i.e., off from the center of the passage direction ms.

The defect information processing unit 73 includes a symmetric judgment unit 75, a coordinates calculation unit 76 and a neighboring image integration unit 77, and these units are configured to perform the following processing.

The symmetric judgment unit 75 determines whether the signal feature C(P) of each pixel output of the sensor pixel P that is successively supplied from the signal feature extraction unit 72 includes signal feature C(P) of the pixel output of the sensor pixel P including the defect image df or not, and then extracts the signal feature C(P) of each pixel output of the sensor pixel P inclining the defect image df. Then the symmetric judgment unit 75 makes a determination on symmetry of the signal features C(P) of the pixel outputs of the sensor pixel P including the defect image df, and extracts the signal feature C(P) of each pixel output of the sensor pixel P at the timing when the center of the defect image df is located at the center of the sensor pixel P in the passage direction ms of the defect image df corresponding to the scanning (primary scanning) of the illumination spot 32 of the sensor pixel P. The symmetric judgment unit 75 makes such a judgment on the symmetry of the signal features C(P) of the pixel outputs of the sensor pixel P including the defect image df, based on whether the signal features C(P) of the pixel outputs of multiple sensor pixels P disposed in a row in the arrangement direction each including the defect image df includes a peak (maximum value) part of the output or not, for example.

In the case of the imaging device 61 illustrated in FIG. 2, including multiple sensor pixels P0, P1, P2 . . . having an isosceles triangle shape that are arranged in the direction vertical to the passage direction ms of the defect image df for the sensor pixel P while reversing the directions of adjacent sensor pixels P in their height direction, the symmetric judgment of the signal features C(P) of the pixel outputs of the sensor pixels P disposed in a row including the defect image df is performed as follows.

In the case 1 of the field 210 where the center of the defect image df passes through the center part in the length direction of the sensor pixel borders q inclined to the passage direction ms over the pixel face of the defect image df without temporarily being inscribed in the sensor pixel borders q1 and q3 defining the mutually facing single pair of oblique lines in the direction vertical to the passage direction ms, the symmetric judgment of the signal features C(P1), C(P2), C(P3) and C(P4) of the pixel outputs can be made based on as to whether all of the signal features C(P1), C(P2), C(P3) and C(P4) of the pixel outputs of the sensor pixels P1, P2, P3 and P4 disposed in a row including the defect image df include a peak (maximum value) part of the pixel output.

In the case 2 of the field 220 where the center of the defect image df passes while temporarily being inscribed in the sensor pixel borders q1 and q3 defining the mutually facing single pair of oblique lines in the direction vertical to the passage direction ms, the symmetric judgment of the signal features C(P1), C(P2) and C(P3) of the pixel outputs can be made based on as to whether all of the signal features C(P1), C(P2) and C(P3) of the pixel outputs of the sensor pixels P1, P2 and P3 disposed in a row including the defect image df include a peak (maximum value) part of the pixel output.

In the case 3 of the field 230 where the center of the defect image df passes through off from the center part in the length direction of the sensor pixel borders q inclined to the passage direction ms over the pixel face of the defect image df toward the entrance in the passage direction without temporarily being inscribed in the sensor pixel borders q1 and q3 defining the mutually facing single pair of oblique lines in the direction vertical to the passage direction ms, the symmetric judgment of the signal features C(P1). C(P2) and C(P3) of the pixel outputs can be made based on as to whether all of the signal features C(P1), C(P2) and C(P3) of the pixel outputs of the sensor pixels P1, P2 and P3 disposed in a row including the defect image df include a peak (maximum value) part of the pixel output.

The above cases 2 and 3 show that the center of the defect image df passes through off from the center part in the length direction of one of the sensor pixel borders q1 and q3 defining the mutually facing single pair of oblique lines in the direction vertical to the passage direction ms toward the entrance in the passage direction of the defect image df, and in the case where the center of the defect image df passes through off from the center to the opposite side not illustrated, i.e., toward the exit in the passage direction as well, the signal features C(P) of the pixel outputs of the sensor pixels P disposed in a row including the defect image df simply have a shape that is line-symmetric about the central part in the length direction of the sensor pixel borders q, and so the symmetric judgment of the signal features C(P) of the pixel outputs of the sensor pixels P disposed in a row including the defect image df can be made similarly to the above cases 2 and 3.

In this way, the symmetric judgment unit 75 confirms the symmetry of the signal features C(P) of the pixel outputs of the sensor pixels P disposed in a row including the defect image df. Then, these signal features C(P) of the sensor pixels P disposed in a row including the defect image df are supplied from the symmetric judgment unit 75 to the coordinates calculation unit 76.

The coordinates calculation unit 76 compares such signal features C(P) of the sensor pixels P disposed in a row including the defect image df, whose symmetry is confirmed by the symmetric judgment unit 75, with a data table stored in the operation basic data storage unit 74 as operation basic data, and calculates a coordinate position of the defect corresponding to the defect image df on the semiconductor wafer 30.

For instance, when the defect inspection tool 1 is used as a surface inspection tool, the coordinates position data is calculated with circle coordinates (r-θ coordinates) where r denotes a distance in the radius direction of the wafer while setting the center of revolving of the semiconductor wafer 30 as the origin and θ denotes variation angle with reference to the revolving standard position. When the defect inspection tool is used as a pattern inspection tool, the coordinates position data is calculated with rectangular coordinates (x-y coordinates) on the wafer surface while setting a predetermined position as the origin.

In the case of the imaging device 61 illustrated in FIG. 2, including multiple sensor pixels P0, P1, P2 . . . having an isosceles triangle shape that are arranged in the direction vertical to the passage direction ms of the defect image df for the sensor pixel P while reversing the directions of adjacent sensor pixels P in their height direction, the coordinates of the defect corresponding to the defect image df on the wafer surface can be calculated as follows, for example.

The signal features C(P), whose symmetry is confirmed by the symmetric judgment unit 75, of the pixel outputs of multiple sensor pixels P shown in the fields of 210, 220 and 230 that are disposed in a row in the arrangement direction, having each pixel face over which the defect image df passes, are signal features C(P) of the pixel outputs of the sensor pixels P in the state of sampling timing when the central position of the sensor pixels P in the passage direction of the defect image df and the center position of the defect image df agree.

Then the coordinates calculation unit 76 can acquire the coordinates position data (θ or x) in the primary scanning direction (R direction or X direction) on the wafer surface of the semiconductor wafer 30 for the defect corresponding to the defect image df based on the sampling timing defined with the sampling rate and the sample time when the signal features C(P1) to C(P4) are extracted, whose symmetry is confirmed by the symmetric judgment unit 75.

Coordinates position data (r or y) in the secondary scanning direction (r direction or Y direction) on the wafer surface of the semiconductor wafer 30 of the defect corresponding to the defect image df can be acquired by detecting, at the oblique sensor pixel borders q1 and q3 of what sensor pixel P and at what position in the passage direction of the defect image df, the center of the defect image passes, i.e., by detecting at what a sampling rate and at what sampling timing the center passes when these signal features C(P1) to C(P4) are extracted.

Then in the cases 1, 2 and 3 indicated in the fields 210, 220 and 230 of FIG. 2, for example, the coordinates calculation unit 76 acquires the coordinates position data (r or y) in the secondary scanning direction (r direction or Y direction) on the wafer surface of the semiconductor wafer 30 of the defect corresponding to the defect image df as follows, based on the cross correlation of the signal features C(P1) to C(P4) of the pixel outputs of the sensor pixels P1 to P4 that are disposed in a row in the arrangement direction, each including the defect image df, whose symmetry is confirmed by the symmetric judgment unit 75.

In the case 1 of the field 210 where the center of the defect image df passes through the center part in the length direction of the sensor pixel borders q inclined to the passage direction ms over the pixel face of the defect image df without temporarily being inscribed in the sensor pixel borders q1 and q3 defining the mutually facing single pair of oblique lines in the direction vertical to the passage direction ms, the signal feature C(P2) of the pixel output of the sensor pixel P2 and the signal feature C(P3) of the pixel output of the sensor pixel P3, and the signal feature C(P1) of the pixel output of the sensor pixel P1 and the signal feature C(P4) of the pixel output of the sensor pixel P4 have a line-symmetric correlation in the mutual pixel output characteristics, which can be represented as a waveform, for a half t½ of the elapsed time t0 to t1 corresponding to the passage time Tp required for the defect image df of the optical resolution (defect size) to pass over the sensor pixel P.

Then, the coordinates calculation unit 76 performs cross correlation operation of the signal features C(P) of the signal features C(P1) to C(P4) of the pixel outputs of the multiple sensor pixels P1 to P4 that are disposed in a row in the arrangement direction, having the pixel surface over each of which the defect image df passes. As a result, the coordinates calculation unit 76 can calculate the coordinates position data (r or y) of the defect corresponding to the defect image df in the secondary scanning direction (r direction or Y direction) on the wafer surface of the semiconductor wafer 30 based on the sampling timing when these signal features C(P1) to C(P4) of the pixel outputs are acquired, and the correlation operation result between the signal features C(P) of the these pixel outputs.

In this case, the coordinates position data (r or y) in the secondary scanning direction (r direction or Y direction) on the wafer surface of the defect corresponding to the defect image df can be calculated by a method of averaging the scanning positions of the centers of the sensor pixels P2 and P3 in the secondary scanning direction (r direction or Y direction) on the wafer surface at this sampling time, for example.

In the case 2 of the field 220 where the center of the defect image df passes while temporarily being inscribed in the sensor pixel borders q1 and q3 defining the mutually facing single pair of oblique lines in the direction vertical to the passage direction ms, the signal feature C(P1) of the pixel output of the sensor pixel P1 and the signal feature C(P3) of the pixel output of the sensor pixel P3, which are arranged on both sides of the sensor pixel P2 where the defect image df is inscribed, have a correlation such that their mutual pixel output characteristics, which can be represented as a waveform, substantially agree.

Then, the coordinates calculation unit 76 performs cross correlation operation of the signal features C(P) of the signal features C(P1) to C(P3) of the pixel outputs of the multiple sensor pixels P1 to P3 that are disposed in a row in the arrangement direction, having the pixel surface over each of which the defect image df passes. As a result, the coordinates calculation unit 76 can calculate the coordinates position data (r or y) of the defect corresponding to the defect image df in the secondary scanning direction (r direction or Y direction) on the wafer surface of the semiconductor wafer 30 based on the sampling timing when these signal features C(P1) to C(P3) of the pixel outputs are acquired, and the correlation operation result between the signal features C(P) of the these pixel outputs.

In this case, the coordinates position data (r or y) of the defect corresponding to the defect image df in the secondary scanning direction (r direction or Y direction) on the wafer surface can be calculated with the scanning position of the center of the sensor pixel P2 in the secondary scanning direction (r direction or Y direction) on the wafer surface at this sampling time, for example.

In the case 3 of the field 230 where the center of the defect image df passes through off from the center part in the length direction of the sensor pixel borders q inclined to the passage direction ms over the pixel face of the defect image df toward the entrance in the passage direction without temporarily being inscribed in the sensor pixel borders q1 and q3 defining the mutually facing single pair of oblique lines in the direction vertical to the passage direction ms, the signal features C(P1), C(P2) and C(P3) of the pixel outputs of the sensor pixels P1, P2 and P3 do not have a special correlation as in the above case 1 or case 2, and the magnitude of the signal features C(P1), C(P2), C(P3) and C(P4) of the pixel outputs and the correlation between the signal features C(P1), C(P2), C(P3) and C(P4) of the pixel outputs change from the correlation as in the above case 1 or case 2.

Then the coordinates calculation unit 76 performs correlation operation of mutual signal features C(P) and each of the signal features C(P) for the features C(P1) to C(P4) of the pixel outputs of the multiple sensor pixels P1 to P4 that are disposed in a row in the arrangement direction, having the pixel faces over each of which the defect image df passes. As a result, the coordinates calculation unit 76 can calculate the coordinates position data (r or y) of the defect corresponding to the defect image df in the secondary scanning direction (r direction or Y direction) on the wafer surface of the semiconductor wafer 30, based on the sampling timing when these signal features C(P1) to C(P4) of the pixel outputs are acquired, and the result of the above correlation operation of the mutual signal features C(P) and each of the signal features C(P) of these pixel outputs.

In this case, the coordinates position data (r or y) of the defect corresponding to the defect image df in the secondary scanning direction (r direction or Y direction) on the wafer surface can be calculated by, for example, calculating a variation of the signal features C(P1), C(P2) and C(P3) of the pixel outputs of the sensor pixels P1, P2 and P3 and of the correlation between the signal features C(P1), C(P2) and C(P3) of the pixel outputs of the pixels P1, P2 and P3 in the case 1 or the case 2 as stated above at this sampling timing, and correcting the scanning position at the center of the sensor pixel P2 in the secondary direction (r direction or Y direction) on the wafer surface at this sampling timing in accordance with this variation.

The above cases 2 and 3 show that the center of the defect image df passes off from the center part in the length direction of one of the sensor pixel borders q1 and q3 defining the mutually facing single pair of oblique lines in the direction vertical to the passage direction ms toward the entrance in the passage direction of the defect image df, and in the case where the center of the defect image df passes through off from the center to the opposite side not illustrated, i.e., toward the exit in the passage direction as well, coordinates position data (r or y) of the defect corresponding to the defect image df in the secondary direction (r direction or Y direction) on the wafer surface can be calculated similarly to the above cases 2 and 3.

In FIG. 1, the neighboring image integration unit 77 adds the signal features C(P) of the pixel outputs of the neighboring sensor pixels P (in the illustrated example, C(P0) and C(P1), C(P1) and C(P2), C(P2) and C(P3), . . . ) among the multiple sensor pixels P (in the illustrated example, P0, P1, P2 . . . ) of the imaging device 61 of each of the optical detectors 60L and 60H that are arranged in the direction vertical to the main scanning direction of the illumination spot 32 on the wafer surface 31, i.e., in the secondary scanning direction of the illumination spot 32 on the wafer surface 31 based on the signal feature C(P) of the pixel output of each sensor pixel P that is supplied successively from the signal feature extraction unit 72 to the defect information processing unit 73. The neighboring image integration unit 77 integrates the thus obtained signal features C(Pm+Pm+1) (m=0, 1, 2, . . . n−1) of the neighboring sensor pixels, thus allowing each of the neighboring sensor pixels to acquire the total amount detected light of the scattered light generated from the wafer surface 31 at the illumination spot, which is detected during the passage time Tp required for the defect image df of the optical resolution (defect size) to pass over one sensor pixel P, i.e., during the sampling time of the defect image df. This total amount of detected light for each of the neighboring sensor pixels is used for estimation of the size of the defect on the wafer surface, for example.

Figure 3:
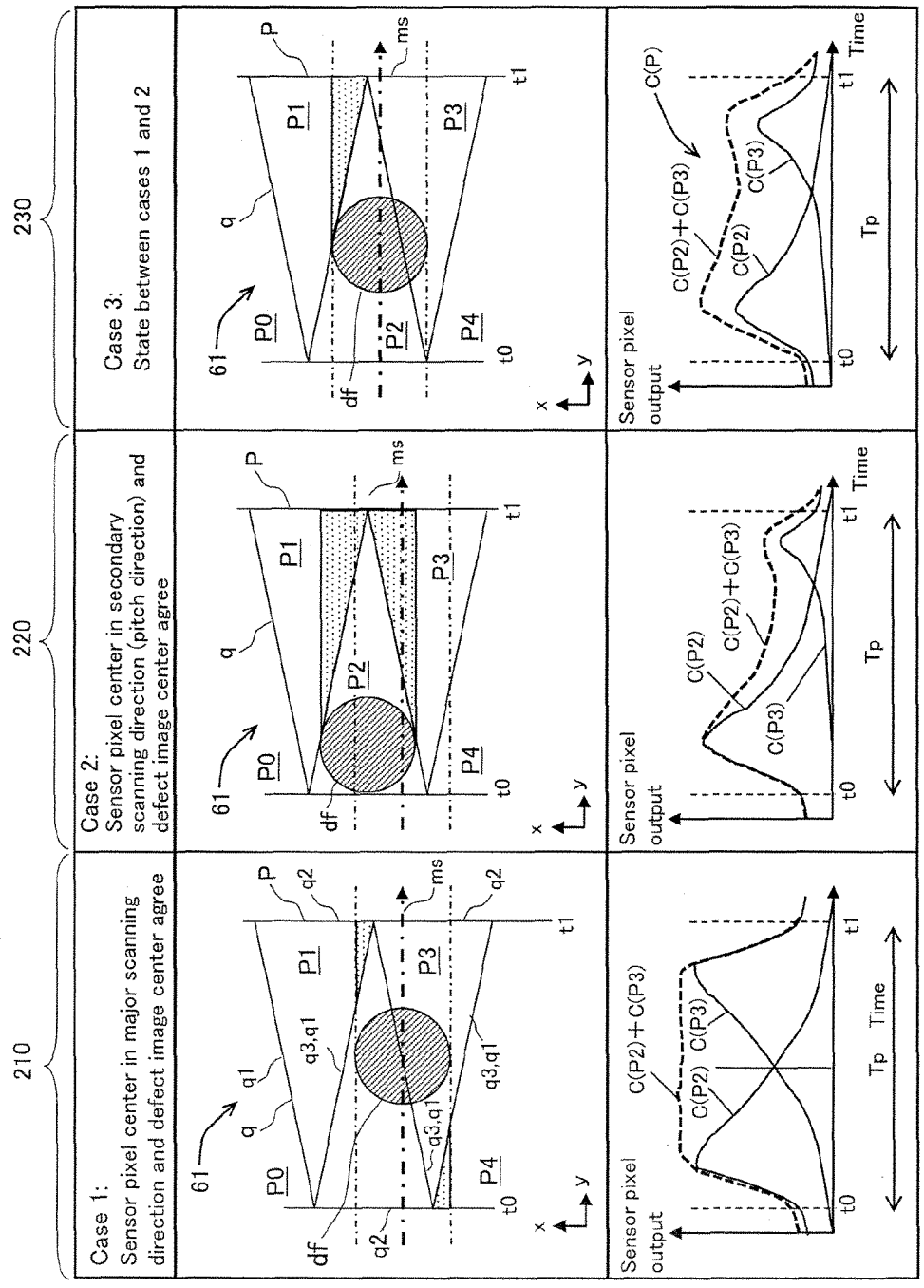
FIG. 3 describes signal feature add operation of the pixel outputs of the neighboring sensor pixels that is performed by a neighboring image integration unit.

FIG. 3 describes signal feature add operation of the pixel outputs of the neighboring sensor pixels that is performed by the neighboring image integration unit.

FIG. 3 illustrates the processing performed by the neighboring image integration unit 77 when the defect image df of the defect of the optical resolution (defect image size) passes through the sensor pixels P0, P1, P2, P3 . . . of the imaging device 61 in each of cases 1, 2 and 3 shown in the fields 210, 220 and 230 of FIG. 2, where the signal features C(P2) and C(P3) of the pixel outputs of the neighboring sensor pixels P2 and P3, for example, are added for integration of the signal features C(P2+P3) of the neighboring sensors pixels P2 and P3. In FIG. 3, like reference numerals designate like parts of FIG. 2, and their descriptions are omitted.

Referring back to FIG. 1, the operation basic data storage unit 74 stores, as operation basic data, operation programs executed at the units 75 to 77 of the defect information processing unit 73 and theoretical value data and actual measurement data used for the execution. For instance, for the calculation of the coordinates position data of a defect on the wafer surface by the coordinates calculation unit 76, a table for operation is stored beforehand as the operation basic data, that stores signal features C(P) of pixel outputs of multiple sensor pixels P that are disposed in a row in the arrangement direction, having the pixel face over which the defect image df passes and which are obtained based on theoretical or actual measurement values beforehand, so as to correspond to the coordinates position data (r or y) in the secondary scanning direction on the wafer surface 31. This allows the coordinates calculation unit 76 to calculate the coordinates position data (r or y) of the defect in the secondary scanning direction easily based on the data matching with this table for operation. Such an operation basic data in a table form as stated above is an example, which can be varied variously. The operation method of the coordinates position of the defect corresponding to the defect image df on the semiconductor wafer 30 by the coordinates calculation unit 76 also can be varied variously based on the features stated in the above cases 1 to 3 for the signal features C(P) of the pixel outputs of multiple sensor pixels P that are disposed in a row in the arrangement direction, through which the defect image df passes over the pixel face.

Such a defect information processing unit 73 including the symmetric judgment unit 75, the coordinates calculation unit 76 and the neighboring image integration unit 77 supplies, as defect information, coordinates position data of the defect corresponding to the defect image df on the wafer surface that is calculated by the coordinates calculation unit 76, the total amount of detected light of the neighboring sensor pixels that is calculated by the neighboring image integration unit 77 and the like to a defect review device not illustrated, for example, and such data is used for defect determination processing.

The defect inspection tool 1 and the imaging device 61 according to the present embodiment are configured as stated above, and their advantageous effects are described below.

The imaging device 61 includes a plurality of sensor pixels P1, P2, P3 . . . having an isosceles triangle shape that are arranged in the direction vertical to the passage direction ms of the defect image df for the sensor pixel P, corresponding to the secondary scanning direction of the illumination spot 32, while reversing the directions of adjacent sensor pixels P in their height direction. Then, each sensor pixel P has the size that is equal to the optical resolution (defect image size) of a defect so as to increase the S/N ration of the pixel output. With this configuration, the defect image df will pass as in the cases 1, 2 and 3 so that the center of the defect image df passes through the sensor pixel border q that is inclined in the direction vertical to the passage direction ms of the defect image df, i.e., in the secondary scanning direction of the illumination spot 32 in any of the passage cases.

As a result, under the control by the control signal generator 80, the symmetric judgment unit 75 of the detection signal processor 70 checks the symmetry of the signal features C(P) of the pixel outputs of the sensor pixels P that are disposed in a row including the defect image df based on the signal features C(P) of the pixel outputs of the sensor pixels P that is supplied successively from the signal feature extraction unit 72, and the coordinates calculation unit 76 can detect the coordinates position of the defect corresponding to the defect image df on the semiconductor wafer 30 using the cross relation of the signal features C(P) or the like based on the thus confirmed signal features C(P) of the pixel outputs of the sensor pixels P.

This enables precise detection of the coordinates position of the defect corresponding to the defect image df on the semiconductor wafer 30 even when the position where the defect image df passes changes with reference to the sensor pixels P on the imaging device 61 in the direction (secondary scanning direction of the illumination spot 32) vertical to primary the scanning direction (passage direction of the defect image).

At this time, as in the case 2 shown in the field 220 of FIG. 2, the state where the center of the defect image df passes through the center of the sensor pixel P between neighboring sensor pixels P can be discriminated based on the signal features (detected signal waveform) C(P) of the neighboring sensor pixels P on both sides, and so the detection reproducibility of the detected signal waveform of the defect image and the defect can be improved because of the signal features (detected signal waveform) C(P) of the sensor pixel P between these neighboring sensor pixels P.

Then, as in the case 1 shown in the field 210 of FIG. 2, the state where the center of the defect image df passes through the center in the scanning direction (passage direction of the defect image) of the sensor pixel P can be discriminated based on the signal features (detected signal waveform) C(P) of mutually adjacent sensor pixels P, and so the detected signal waveform of the defect image and the defect when the center of the defect image df passes through the center in the scanning direction (passage direction of the defect image) can be reproduced, and the detection reproducibility can be accordingly improved.

Further as in the case 3 shown in the field 230 of FIG. 2, in the case where the defect image df is not inscribed in the sensor pixel borders q1 and q3 with the neighboring sensor pixels P on both sides, and so the center of the defect image df does not pass through the center in the scanning direction (passage direction of the defect image) of the sensor pixel P as well, the coordinates position of the defect corresponding to the defect image df on the semiconductor wafer 30 can be found or the detected signal waveform of the defect image and the defect can be reproduced by mainly using the pixel P having the maximum S/N ratio, which is the ratio of the background noise component (scattered light component resulting from the roughness of the wafer surface or white noise) included in the scattered light detection signal from the optical detectors 60L, 60H among the neighboring sensor pixels P on both sides and a sensor pixel between these neighboring sensor pixels, whereby the sensitivity of the defect detection can be improved.

Figure 4:
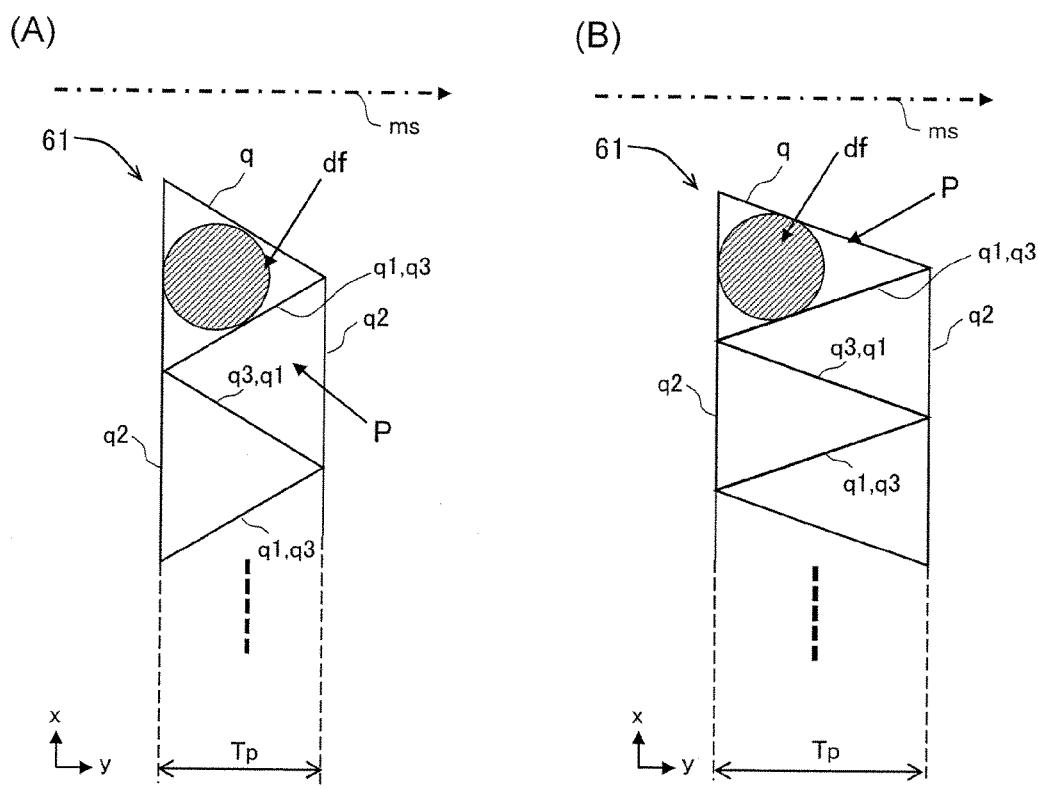
FIG. 4 describes a variation of the sensor pixel having an isosceles triangle shape used in the imaging device of FIG. 2.

FIG. 4 describes a variation of the sensor pixel having an isosceles triangle shape used in the imaging device of FIG. 2.

This sensor pixel P has a regular triangle shape or an isosceles triangle shape having the size circumscribing the defect image df, in which the defect image df of the optical resolution that is at a diffraction limit (optical resolution: $0.61*\lambda/NA$, $\lambda$: illumination wavelength, NA: lens aperture) can be inscribed.

Each shape has sensor pixel borders q1 and q3 defining a single pair of oblique lines on the pixel face of the sensor pixel P as well as a bottom side q2, in all of which the defect image is inscribed, so as to maximize the S/N ratio that is a ratio between the background noise component and the signal component.

The sensor pixel P in FIG. 4(A) can enlarge the length of the detection face of the imaging device 61 along the direction vertical to the passage direction ms without increasing the number of pixels of the sensor pixel P and without decreasing the S/N ratio when multiple sensor pixels P are arranged in the direction vertical to the passage direction ms of the defect image df for the sensor pixels P, i.e., in the secondary scanning direction of the illumination spot 32.

The sensor pixel P in FIG. 4(B) can increase the passage time Tp required for the defect image df of the optical resolution (defect size) to pass over one sensor pixel P in synchronization with the scanning of the illumination spot 32 (primary scanning), i.e., the sampling time of the defect image df.

Figure 5:
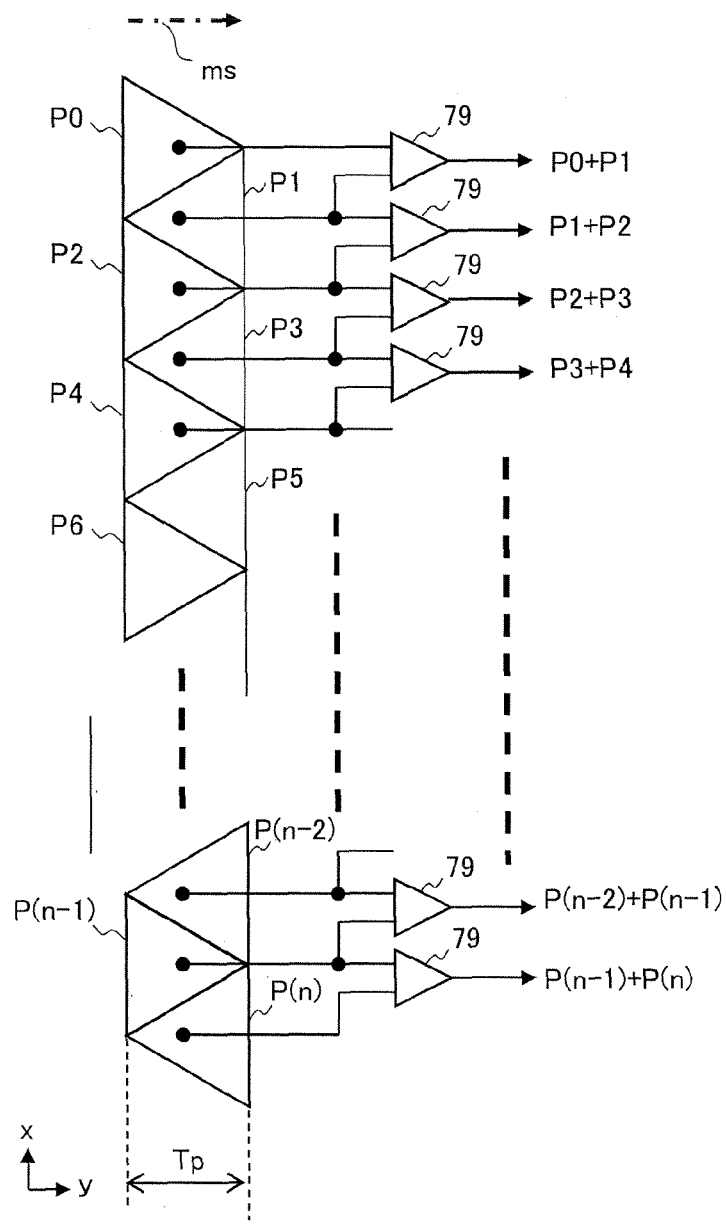
FIG. 5 describes a variation to reduce the scale of signal processing by a defect information processing unit.

FIG. 5 describes a variation to reduce the scale of signal processing by the defect information processing unit.

The illustrated configuration is such that the processing to add the signal features C(P) of the pixel outputs of the neighboring sensor pixels P among the signal processing performed by the neighboring image integration unit 77 of the defect information processing unit 73 is performed by the signal feature extraction unit 72 outside the defect information processing unit 73 so as not to make the signal processing by the defect information processing unit 73 of the detection signal processor 70 heavier than the signal processing by the signal feature extraction unit 72.

FIG. 5 represents the configuration of the signal feature extraction unit 72 to successively fetch a digitized scattered light detected signal supplied from the A/D converter 71 and divide the pixel outputs of the multiple sensor pixels P into each sensor pixel P with each of the multiple sensor pixels P.

In the illustrated example, adders (addition circuits) 79 to add the pixel outputs of the neighboring sensor pixels P(m) and P(m+1) is provided in the signal feature extraction unit 72. This allows the signal feature extraction unit 72 to supply the signal feature C (Pm+Pm+11) of the neighboring sensor pixels as well to the defect information processing unit 73 similarly to the signal feature C(P) of the pixel outputs of the neighboring sensor pixels P.

In this way, the defect information processing unit 73 can directly fetch the signal feature C(Pm+Pm+1) (m=0, 1, 2, . . . , n−1) of the neighboring sensors from the signal feature extraction unit 72, and so the neighboring image integration unit 77 simply has to perform the integration processing, and so the scale of the signal processing by the defect information processing unit 73 can be reduced. As a result, sampling rate for the pixel outputs of the multiple sensor pixels P increases depending on the performance required for the defect inspection tool 1, and so processing can be performed even for extended sampling time.

In the illustrated example, the signal feature extraction unit 72 of the detection signal processor 70 performs the processing of adding the pixel outputs of the neighboring sensor pixels P(m), P(m+1) using the adders 79. Instead of the detection signal processor 70, the optical detectors 60L and 60H, which send out scattered light detected signal that are pixel outputs of the sensor pixels P, may be provided with adders similarly for such processing.

Embodiment 2

Figure 6:
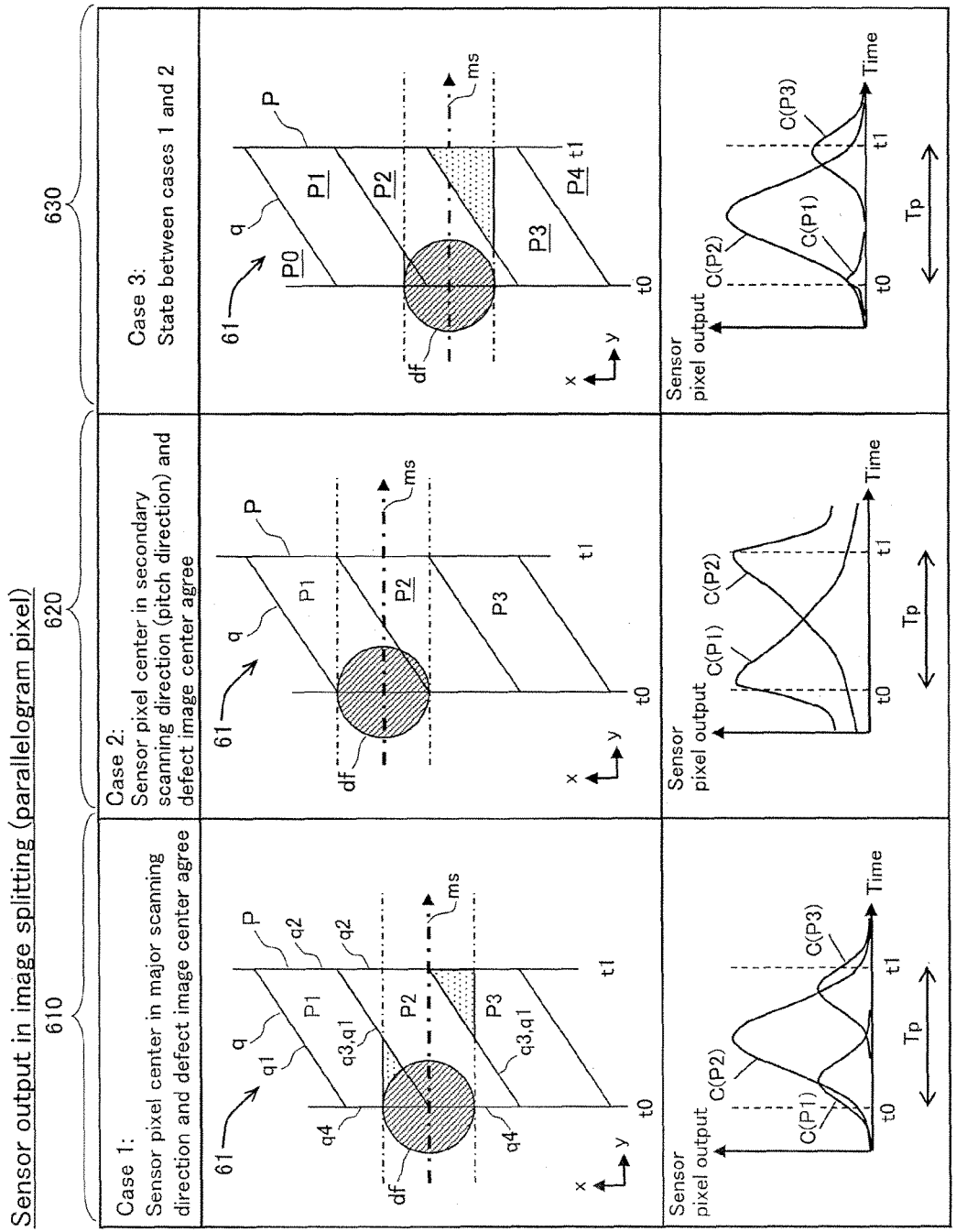
FIG. 6 shows the configuration of an imaging device of an optical detector that is used for the defect inspection tool according to Embodiment 2 of the present invention, and describes how to detect a defect by the defect inspection tool.

FIG. 6 shows the configuration of an imaging device of an optical detector that is used for the defect inspection tool according to Embodiment 2 of the present invention, and describes how to detect a defect by the defect inspection tool.

Similarly to the defect inspection tool 1 according to Embodiment 1 in FIG. 1, the defect inspection tool 1 according to the present embodiment includes a light source 10, illumination optics 20L, 20H, a stage mechanism 40, imaging optics 50L, 50H, optical detectors 60L, 60H and a detection signal processor 70 and a control signal generator 80, and is different in the configuration of an imaging device 61 of each of the optical detectors 60L, 60H only. In the following description, like reference numerals designate like parts of the defect inspection tool 1 according to Embodiment 1, and their duplicated descriptions are omitted.

As illustrated in FIG. 6, each sensor pixel P0, P1, P2, P3 . . . of the imaging device 61 of the present embodiment has the same basic configuration of each sensor pixel P0, P1, P2, P3 . . . in FIG. 1, i.e., being configured so that among at least three sensor pixel borders q of one sensor pixel P, at least one of a pair of sensor pixel borders q that are opposed in the arrangement direction of the sensor pixels P that is vertical to the passage direction ms of the defect image df to the sensor pixels P on the sensor pixels is inclined to the primary scanning direction (R direction or X direction) of the illumination spot 32, but each sensor pixel P has a parallelogram shape.

In the illustrated example, four sensor pixel borders q defining one sensor pixel P having a parallelogram shape include a pair of parallel opposite sides q2 and q4 that are parallel to the direction vertical to the passage direction ms of the defect image df to the sensor pixels P, and a pair of opposite sides q1 and q3 that are inclined to the passage direction ms of the defect image df to the sensor pixels P.

The parallelogram of each sensor pixel P has a shape and a size such that the pair of opposite sides q2 and q4 that are parallel to the direction vertical to the passage direction ms of the defect image df to the sensor pixels P has a length that is equal to the width (diameter) Ddf of the defect image df of the optical resolution in the same direction, i.e., in the secondary scanning direction (r direction or Y direction) of the illumination spot 32, and one of a pair of diagonal lines is parallel to the passage direction ms.

In the case of the imaging device 61 illustrated in FIG. 6, including multiple sensor pixels P0, P1, P2 . . . having a parallelogram shape that are arranged in the direction vertical to the passage direction ms of the defect image df for the sensor pixel P, the symmetric judgment unit 75 makes a symmetric judgment of the signal features C(P) of the pixel outputs of the sensor pixels P disposed in a row including the defect image df as follows.

In the case 1 of the field 610 where the center of the defect image df passes along the diagonal line of the sensor pixel P2 having a parallelogram shape that is parallel to the passage direction ms of the defect image df, i.e., the center passes through the center of the sensor pixel P2, the symmetric judgment of the signal features C(P1), C(P2) and C(P3) of the pixel outputs can be made based on as to whether all of the signal features C(P1), C(P2) and C(P3) of the pixel outputs of the sensor pixels P1, P2 and P3 disposed in a row including the defect image df include a peak (maximum value) part of the pixel output.

In the case 2 of the field 620 where the center of the defect image df passes through a central part in the length direction of the sensor pixel border q3 (q1) of the sensor pixel P2(P3) that is inclined to the passage direction ms of the defect image df over the pixel face, the symmetric judgment of the signal features C(P1) and C(P2) of the pixel outputs can be made based on as to whether the signal features C(P1) and C(P2) of the pixel outputs of the sensor pixels P1 and P2 disposed in a row including the defect image df include a peak (maximum value) part of the pixel output.

In the case 3 of the field 630 where the center of the defect image df passes through off from the center part in the length direction of the sensor pixel border q3 (q1) that is inclined to the passage direction ms of the defect image df over the pixel face toward the exit in the passage direction, the symmetric judgment of the signal features C(P1), C(P2) and C(P3) of the pixel outputs can be made based on as to whether all of the signal features C(P1), C(P2) and C(P3) of the pixel outputs of the sensor pixels P1, P2 and P3 disposed in a row including the defect image df include a peak (maximum value) part of the pixel output.

The above cases 1 and 3 show that the center of the defect image df passes through off from the center part in the length direction of the sensor pixel border q3 (q1) of the sensor pixel P2(P3) that is inclined to the passage direction ms of the defect image df over the pixel face toward the exit in the passage direction, and in the case where the center of the defect image df passes through off from the center to the opposite side not illustrated, i.e., toward the entrance in the passage direction as well, the signal features C(P) of the pixel outputs of the sensor pixels P disposed in a row including the defect image df simply have a shape that is line-symmetric about the central part in the length direction of the sensor pixel borders q, and so the symmetric judgment of the signal features C(P) of the pixel outputs of the sensor pixels P disposed in a row including the defect image df can be made similarly to the above cases 1 and 3.

In this way, the symmetric judgment unit 75 confirms the symmetry of the signal features C(P) of the pixel outputs of the sensor pixels P disposed in a row, including the defect image df. Then, these signal features C(P) of the sensor pixels P disposed in a row including the defect image df are supplied from the symmetric judgment unit 75 to the coordinates calculation unit 76.

The coordinates calculation unit 76 compares such signal features C(P) of the sensor pixels P disposed in a row including the defect image df, whose symmetry is confirmed by the symmetric judgment unit 75, with a data table stored in the operation basic data storage unit 74 as operation basic data, and calculates a coordinate position of the defect corresponding to the defect image df on the semiconductor wafer 30.

For instance, when the defect inspection tool 1 is used as a surface inspection tool, the coordinates position data is calculated with circle coordinates (r-θ coordinates) where r denotes a distance in the radius direction of the wafer while setting the center of revolving of the semiconductor wafer 30 as the origin and θ denotes variation angle with reference to the revolving standard position. When the defect inspection tool is used as a pattern inspection tool, the coordinates position data is calculated with rectangular coordinates (x-y coordinates) on the wafer surface while setting a predetermined position as the origin.

In the case of the imaging device 61 illustrated in FIG. 6, including multiple sensor pixels P0, P1, P2 . . . having a parallelogram shape that are arranged in the direction vertical to the passage direction ms of the defect image df for the sensor pixel P, the coordinates calculation unit 76 can calculate the coordinates of the defect corresponding to the defect image df on the wafer surface as follows, for example.

The signal features C(P), whose symmetry is confirmed by the symmetric judgment unit 75, of the pixel outputs of multiple sensor pixels P shown in the fields of 610, 620 and 630 that are disposed in a row in the arrangement direction, having each pixel face over which the defect image df passes, are signal features C(P) of the pixel outputs of the sensor pixels P in the state of sampling timing when the central position of the sensor pixels P in the passage direction of the defect image df and the center position of the defect image df agree.

Then the coordinates calculation unit 76 can acquire the coordinates position data (θ or x) in the primary scanning direction (R direction or X direction) on the wafer surface of the semiconductor wafer 30 for the defect corresponding to the defect image df based on the sampling timing defined with the sampling rate and the sample time when the signal features C(P1) to C(P3) are extracted, whose symmetry is confirmed by the symmetric judgment unit 75.

Coordinates position data (r or y) in the secondary scanning direction (r direction or Y direction) on the wafer surface of the semiconductor wafer 30 of the defect corresponding to the defect image df can be acquired by detecting, at the oblique sensor pixel borders q1 and q3 of what sensor pixel P and at a what position in the passage direction of the defect image df, the center of the defect image passes, i.e., detecting at what a sampling rate and at what sampling timing the center passes when these signal features C(P1) to C(P3) are extracted.

Then in the cases 1, 2 and 3 indicated in the fields 610, 620 and 630 of FIG. 6, for example, the coordinates calculation unit 76 acquires the coordinates position data (r or y) in the secondary scanning direction (r direction or Y direction) on the wafer surface of the semiconductor wafer 30 of the defect corresponding to the defect image df as follows, based on the cross correlation of the signal features C(P1) to C(P3) of the pixel outputs of the sensor pixels P1 to P3 that are disposed in a row in the arrangement direction, having a pixel face over which the defect image df passes, whose symmetry is confirmed by the symmetric judgment unit 75.

In the case 1 of the field 610 where the center of the defect image df passes along the diagonal line of the sensor pixel P2 having a parallelogram shape that is parallel to the passage direction ms of the defect image df, the signal feature C(P1) of the pixel output of the sensor pixel P1 and the signal feature C(P3) of the pixel output of the sensor pixel P3 that are arranged on both sides of the sensor pixel P2 have a line-symmetric correlation in the mutual pixel output characteristics, which can be represented as a waveform, for a half t½ of the elapsed time t0 to t1 corresponding to the passage time Tp required for the defect image df of the optical resolution (defect size) to pass over the sensor pixel P.

Then, the coordinates calculation unit 76 performs cross correlation operation of the signal features C(P) of the signal features C(P1) to C(P3) of the pixel outputs of the multiple sensor pixels P1 to P3 that are disposed in a row in the arrangement direction, having the pixel surface over each of which the defect image df passes. As a result, the coordinates calculation unit 76 can calculate the coordinates position data (r or y) of the defect corresponding to the defect image df in the secondary scanning direction (r direction or Y direction) on the wafer surface of the semiconductor wafer 30 based on the sampling timing when these signal features C(P1) to C(P3) of the pixel outputs are acquired, and the correlation operation result between the signal features C(P) of the these pixel outputs.

In this case, the coordinates calculation unit 76 can calculate the coordinates position data (r or y) of the defect corresponding to the defect image df in the secondary scanning direction (r direction or Y direction) on the wafer surface with the scanning position of the center of the sensor pixel P2 in the secondary scanning direction (r direction or Y direction) on the wafer surface at this sampling time, for example.

In the case 2 of the field 620 where the center of the defect image df passes through a central part in the length direction of the sensor pixel border q3 (q1) of the sensor pixel P2(P3) that is inclined to the passage direction ms of the defect image df over the pixel face, the signal feature C(P2) of the pixel output of the sensor pixel P2 and the signal feature C(P3) of the pixel output of the sensor pixel P3 have a line-symmetric correlation in the mutual pixel output characteristics, which can be represented as a waveform, for a half t½ of the elapsed time t0 to t1 corresponding to the passage time Tp required for the defect image df of the optical resolution (defect size) to pass over the sensor pixel P.

Then, the coordinates calculation unit 76 performs cross correlation operation of the signal features C(P) of the signal features C(P1) to C(P3) of the pixel outputs of the multiple sensor pixels P1 to P3 that are disposed in a row in the arrangement direction, having the pixel surface over each of which the defect image df passes. As a result, the coordinates calculation unit 76 can calculate the coordinates position data (r or y) of the defect corresponding to the defect image df in the secondary scanning direction (r direction or Y direction) on the wafer surface of the semiconductor wafer 30 based on the sampling timing when these signal features C(P1) to C(P3) of the pixel outputs are acquired, and the correlation operation result between the signal features C(P) of the these pixel outputs.

In this case, the coordinates calculation unit can calculate the coordinates position data (r or y) of the defect corresponding to the defect image df in the secondary scanning direction (r direction or Y direction) on the wafer surface by averaging the scanning positions of the centers of the sensor pixels P2 and P3 in the secondary scanning direction (r direction or Y direction) on the wafer surface at this sampling time, for example.

In the case 3 of the field 630 where the center of the defect image df passes through off from the center part in the length direction of the sensor pixel border q3 (q1) of the sensor pixel P2(P3) that is inclined to the passage direction ms of the defect image df over the pixel face toward the exit in the passage direction, the signal features C(P1), C(P2) and C(P3) of the pixel outputs of the sensor pixels P1, P2 and P3 do not have a special correlation as in the above case 1 or case 2, and the magnitude of the signal features C(P1), C(P2) and C(P3) of the pixel outputs and the correlation between the signal features C(P1), C(P2) and C(P3) of the pixel outputs change from the correlation as in the above case 1 or case 2.

Then the coordinates calculation unit 76 performs correlation operation of mutual signal features C(P) and each of the signal features C(P) for the features C(P1) to C(P3) of the pixel outputs of the multiple sensor pixels P1 to P3 that are disposed in a row in the arrangement direction, having the pixel faces over each of which the defect image df passes. As a result, the coordinates calculation unit 76 can calculate the coordinates position data (r or y) of the defect corresponding to the defect image df in the secondary scanning direction (r direction or Y direction) on the wafer surface of the semiconductor wafer 30, based on the sampling timing when these signal features C(P1) to C(P3) of the pixel outputs are acquired, and the result of the above correlation operation of the mutual signal features C(P) and each of the signal features C(P) of these pixel outputs.

In this case, the coordinates position data (r or y) of the defect corresponding to the defect image df in the secondary scanning direction (r direction or Y direction) on the wafer surface can be calculated by, for example, calculating a variation of the signal features C(P1), C(P2) and C(P3) of the pixel outputs of the sensor pixels P1, P2 and P3 and of the correlation between the signal features C(P1), C(P2) and C(P3) of the pixel outputs of the pixels P1, P2 and P3 in the case 1 or the case 2 as stated above at this sampling timing, and correcting the scanning position at the center of the sensor pixel P2 in the secondary direction (r direction or Y direction) on the wafer surface at this sampling timing in accordance with this variation.

The above cases 3 and 1 show that the center of the defect image df passes off from the center part in the length direction of one of the sensor pixel borders q1 and q3 defining the mutually facing single pair of oblique lines in the direction vertical to the passage direction ms toward the exit in the passage direction of the defect image df, and in the case where the center of the defect image df passes through off from the center to the opposite side not illustrated, i.e., toward the entrance in the passage direction as well, coordinates position data (r or y) of the defect corresponding to the defect image df in the secondary direction (r direction or Y direction) on the wafer surface can be calculated similarly to the above cases 2 and 3.

The thus configured defect inspection tool 1 and the imaging device 61 according to the present embodiment, similarly to the defect inspection tool 1 and the imaging device 61 according to Embodiment 1, enable precise detection of the coordinates position of the defect corresponding to the defect image df on the semiconductor wafer 30 even when the position where the defect image df passes changes with reference to the sensor pixels P on the imaging device 61 in the direction (secondary scanning direction of the illumination spot 32) vertical to the scanning direction (passage direction of the defect image) and so the amount of light detected of one sensor pixel P of the scattered light generated from the defect of the optical resolution (defect size) irradiated with the illumination beam changes. Further, the detection reproducibility of the detected signal waveform of the defect image and the defect can be improved, and the defect detection sensitivity also can be improved.

Embodiment 3

In FIG. 1, the defect inspection tool 1 according to Embodiments 1 and 2 is configured so that the detection signal processor 70 includes the A/D converter 71, the signal feature extraction unit 72, the defect information processing unit 73 and the operation basic data storage unit 74. On the other hand, a defect inspection tool 1 according to the present embodiment includes the signal feature extraction unit 72, to which is a noise threshold storage unit 78 is installed.

The signal feature extraction unit 72 of the defect inspection tool 1 is configured to remove a background noise component from the pixel outputs of the sensor pixels P that are successively fetched via the A/D converter 71 based on a noise threshold THn stored in the noise threshold storage unit 78, which is for avoiding a calculation error occurring at the defect information processing unit 73 due to the background noise component included in the pixel outputs of the sensor pixels P that are supplied from the optical detectors 60L, 60H as a scattered light detection signal when the signal features of the pixel outputs of each sensor pixel P is supplied to the operation basic data storage unit 74, and then generate a signal feature C(P) of the pixel output for each sensor pixel P.

Figure 7:
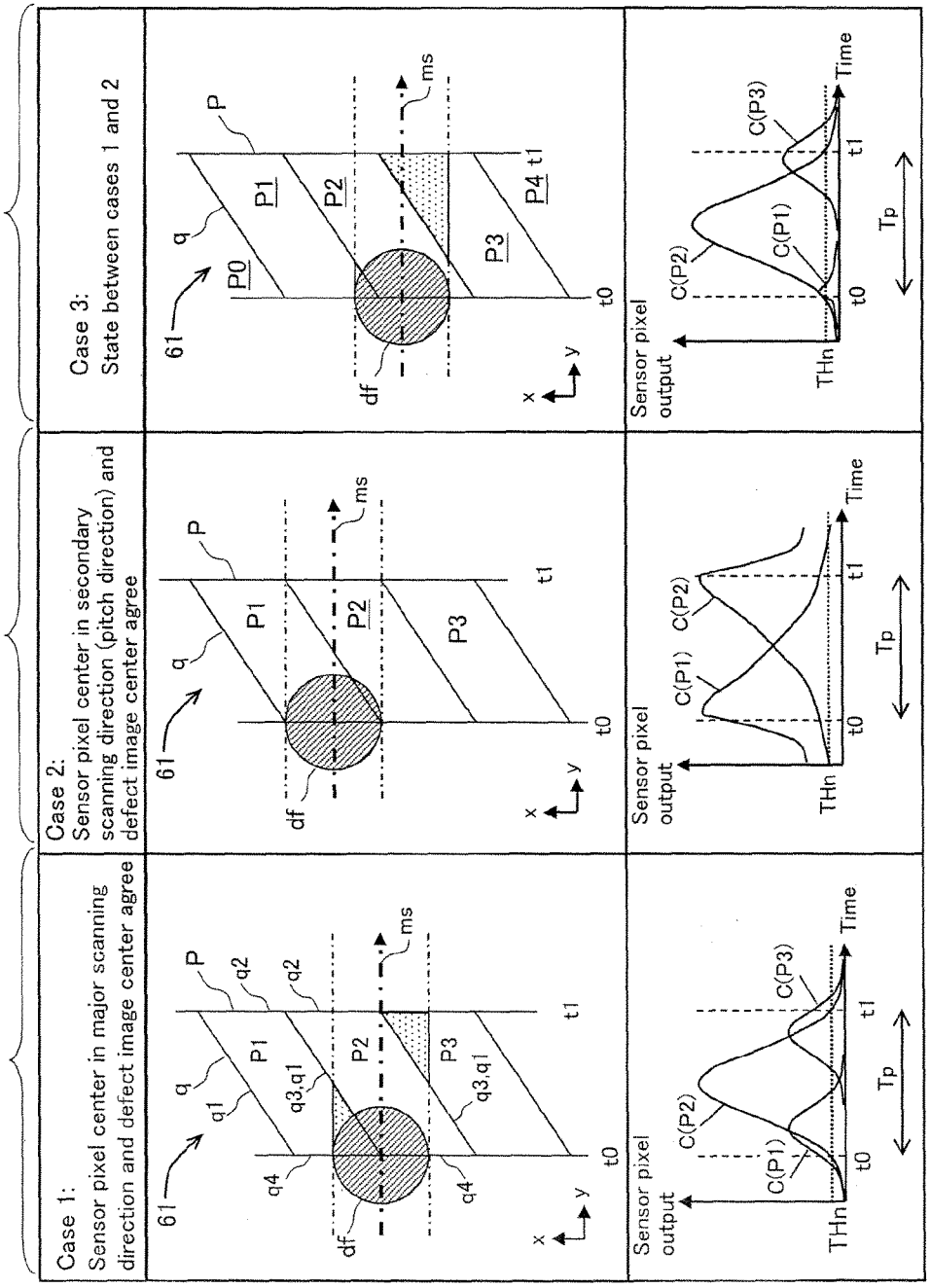
FIG. 7 describes the background noise removal processing, which is performed by a signal feature extraction unit that is used for a defect inspection tool according to Embodiment 3 of the present invention.

FIG. 7 describes the background noise removal processing to remove a background noise component from the pixel output of each pixel P, which is performed by the signal feature extraction unit.

FIG. 7 illustrates the state of, when a defect image df of a defect of the optical resolution (defect image size) in each of the cases 1, 2 and 3 shown in the fields 610, 620 and 630 of FIG. 6 passes over sensor pixels P0, P1, P2, P3 . . . of the imaging device 61, removing a background noise component from the pixel output of each sensor pixel P and generating a signal feature C(P) of the pixel output for each sensor pixel P. In FIG. 7, like reference numerals designate like parts of FIG. 6, and their descriptions are omitted.

As illustrated in FIG. 7, the signal feature C(P) of the pixel output for sensor pixel P, from which a background noise component is removed, is a signal obtained by removing a signal feature part that is the noise threshold THn or lower from the signal features C(P1), C(P2), C(P3), . . . of the pixel outputs of the sensor pixels P before the removal of noise components, meaning a pixel output part (part of the amount of output light) that is the noise threshold or more in the pixel output of the sensor pixel P before the removal of the background noise component.

Embodiment 4

FIG. 8 illustrates the configuration of an imaging device, which is applied to a defect inspection tool according to the present embodiment.

The defect inspection tool according to the present embodiment has a configuration similar to that of the defect inspection tool 1 of FIG. 1, and is different in the configuration of sensor pixels of the imaging device 61 only.

As illustrated in FIG. 8, each sensor pixel P of the imaging device that is applied to the defect inspection tool 1 according to the present embodiment has a shape different from the sensor pixel P having a parallelogram shape of the imaging device 61 of FIG. 6, and has a shape of a parallelogram shape having the size circumscribing the defect image df, in which the defect image df of the optical resolution that is at a diffraction limit (optical resolution: $0.61*\lambda/NA$, $\lambda$: illumination wavelength, NA: lens aperture) can be inscribed.

Similarly to the sensor pixels P having an isosceles triangle shape of FIG. 4, the sensor pixels P illustrated in FIGS. 8(A) to (C) have shapes and sizes such that, when the defect image df of the optical resolution (defect size) passes over the pixel face along the passage direction ms shown in the drawing, and when the center of the defect df passes through the center of the pixel face, the defect image df is temporarily inscribed in all sensor pixel borders q1, q2, q3 and q4, and at the time of this inscription, the defect df is entirely overlapped on the pixel face of the sensor pixel P.

At the time of such inscription of the defect image df, the sensor pixels P having a parallelogram shape illustrated in FIGS. 8(A) to (C) includes a pair of sensor pixel borders q2 and q4 that are vertical to the passage direction ms and are mutually opposed in the passage direction ms, and the defect image comes into contact with such sensor pixel borders q2 and q4 as well. This means that the center of the defect image df and the center of the pixel face of the sensor pixel P agree. Then, when the imaging device 61 include a plurality of such sensor pixels P that are arranged in the direction vertical to the passage direction ms of the defect image df to the sensor pixels P, i.e., in the secondary scanning direction of the illumination spot 32, as the passage position of the center of the defect image df is displaced from the inscription position along the direction vertical to the passage direction ms, i.e., along the secondary scanning direction of the illumination spot 32, the pixel output from one sensor pixel P can be changed in accordance with the amount of the displacement. This can speed up the sending of the illumination spot 32 in the secondary scanning direction.

In such a case as well, the sensor pixel P illustrated in FIG. 8(B) can enlarge the length of the detection face of the imaging device 61 along the direction vertical to the passage direction ms without increasing the number of pixels of the sensor pixel P and without decreasing the S/N ratio when multiple sensor pixels P are arranged in the direction vertical to the passage direction ms of the defect image df for the sensor pixels P, i.e., in the secondary scanning direction of the illumination spot 32. The sensor pixel P illustrated in FIG. 8(C) can maximize the S/N ratio that is the ratio between the background noise component and the signal component.

On the other hand, a sensor pixel P having a parallelogram shape of FIG. 8(D) is not restricted so that the center of the sensor pixel P is to be placed on the diagonal line parallel to the passage direction ms of the defect unlike the sensor pixel P having a parallelogram of FIG. 6 as long as the defect image df is inscribed in between the pair of opposite sides q2 and q4 that are parallel to the direction vertical to the passage direction ms. This can increase the passage time Tp required for the defect image df of the optical resolution (defect size) to pass over one sensor pixel P in synchronization with the scanning of the illumination spot 32 (primary scanning), i.e., the sampling time of the defect image df.

Embodiment 5

FIG. 9 describes one embodiment to reduce the scale of signal processing by the defect inspection tool.

In FIG. 9, the defect inspection tool 1 including the optical detectors 60L and 60H provided with the imaging device 61 of FIG. 2 made up of multiple sensor pixels P0, P1, P2 . . . having an isosceles triangle shape that are arranged in the direction vertical to the passage direction ms of the defect image df for the sensor pixel P while reversing the directions of adjacent sensor pixels P in their height direction is configured to function as the defection inspection tool 1 including the optical detectors 60L and 60H provided with the imaging device 61 of FIG. 8 made up of multiple sensor pixels P0, P1, P2 . . . having a parallelogram shape that are arranged in the direction vertical to the passage direction ms of the defect image df for the sensor pixel P.

The defect inspection tool 1 according to the present embodiment has the configuration similar to that of the defect inspection tool 1 of FIG. 1, including the optical detectors 60L and 60H provided with the imaging device 61 of FIG. 2 made up of multiple sensor pixels P0, P1, P2 . . . having an isosceles triangle shape that are arranged in the direction vertical to the passage direction ms of the defect image df for the sensor pixel P while reversing the directions of adjacent sensor pixels P in their height direction, which is different in the sending-out configuration of a scatter light detected signal to the detection signal processor 70.

As illustrated in FIG. 9, the optical detectors 60L, 60H are provided with an adder 63 to add the pixel outputs of adjacent sensor pixels P. This allows sensor pixels P0, P1, P2 . . . having an isosceles triangle shape to function as sensor pixels Pm·m+1, Pm+1·m+2 (where, m=0, 1, 2, . . . n−2) having a parallelogram shape including the bottom sides of the adjacent sensor pixels P0, P1, P2 . . . each having an isosceles triangle shape as a pair of opposite sides.

This can configure the imaging device 61 including sensor pixels Pm·m+1, Pm+1·m+2 having two types of parallelogram shapes, whose pixel areas are overlapped in their halves and having a pair of opposed sides with different oblique directions to the passage direction ms of the defect image, which are arranged in the direction vertical to the passage direction ms of the defect image, and so the scale of the signal processing by the defect information processing unit 73 can be decreased in the system configuration, while performance such as the detection sensitivity and the detection reproducibility can be ensured because of the passage position of the detect image over the sensor pixels Pm·m+1, Pm+1·m+2.

In the illustrated example, the adder is provided on the sides of the optical detectors 60L and 61H similarly, thus forming the sensor pixels Pm·m+1, Pm+1·m+2 (where, m=0, 1, 2, . . . n−2) having a parallelogram shape. Alternatively, the signal feature extraction unit 72 of the detection signal processor 70 may perform the adding using the adder 63.

Embodiment 6

FIG. 10 describes a defect inspection tool including an optical detector provided with an imaging device of single pixel of a size that is larger than the optical resolution (defect size).

The defect inspection tool 1 includes a imaging device 61 made up of two sensor pixels P1 and P2 each having a rectangular triangle shape that are arranged in the direction vertical to the passage direction ms of the defect image df for the sensor pixel P while reversing the directions of adjacent sensor pixels P in their height direction.

The sensor pixels P1 and P2 each have a pixel face that is larger in size than the optical resolution (defect size). The defect inspection tool 1 has the same configuration and operates in the same manner as the configuration and the operation of the defect inspection tool 1 of Embodiment 1, which is different only in the optical detectors 60L, 60H having the imaging device 61 as stated above.

Similarly to the defect inspection tool 1 and the imaging device 61 according to Embodiment 1, the defect inspection tool 1 of the present embodiment also, having a larger size of the sensor pixels P1 and P2, can detect the coordinate position of the defect corresponding to the defect image df on the semiconductor wafer 30 precisely even when the passage position of the defect image df changes with respect to the sensor pixel P on the imaging device 61 in the direction vertical to the scanning direction (passage direction of the defect image) (secondary scanning direction of the result output unit 32). This can improve the detection reproducibility of the detected signal waveform of the defect image and the defect, and can improve the defect detection sensitivity also.

Further, even when the illuminance distribution of the illumination spot 32 along the secondary scanning direction of the illumination spot 32 is made uniform, the coordinate position of the defect on the semiconductor wafer 30 can be detected precisely, thus eliminating the necessity of overlap scanning of the illumination distribution in a Gaussian distribution. This can improve the inspection throughput, the detection reproducibility and the detection sensitivity.

The following describes the advantageous effects of the defect inspection tool 1 according to the embodiments of the present invention as stated above and of the imaging device 61 applied thereto, in comparison with comparative examples.

Comparative Example 1

FIG. 11 illustrates Comparative Example 1.

An imaging device 611 includes multiple sensor pixels P each having a square shape arranged.

When the sensor pixel P of the imaging device 611 and the optical resolution (defect image size) of a defect are equivalent in size, if the passage position of the defect image df changes in the direction vertical to the scanning direction with reference to the sensor pixel P on the imaging device 611, the pixel output thereof also changes, and the S/N ratio of the detected image of the defect also changes. For instance, when the center of the defect image df does not agree with the central part of the sensor pixel P of the imaging device 611, and a part of the defect image P1 only passes over the sensor pixel in the state where the center of the defect image df agrees with the border part between the sensor pixel P1 and the adjacent sensor pixel P2, then the S/N ratio of the pixel output of this sensor pixel P deteriorates to ½.

Comparative Example 2

FIG. 12(A) illustrates Comparative Example 2.

As illustrated in FIG. 12(A), this example is configured so that a pixel has a dimension ry/2 that is a half of the pixel size dimension ry of the imaging device 611 of FIG. 11 along the direction vertical to the passage direction of the defect image df, and pixel outputs of the adjacent sensor pixels is averaged for the adjacent pixel averaging processing. In this case, the S/N ratio of the pixel output of each sensor pixel P can be improved to be $1(\sqrt{2})$. However, this processing makes the optical resolution of the defect to be ½, and the resolved defect will have a size that is twice of the actual size.

Comparative Example 3

FIG. 12(B), (C) illustrates Comparative Example 3.

As illustrated in FIG. 12(B), (C), when the imaging device 611 includes a single sensor pixel, and when the pixel size ry is too large compared with the optical resolution of the defect, the position of the defect df on the wafer surface cannot be detected without overlap scanning of the illumination spot 32 of the illumination distribution having a Gaussian distribution, even when the S/N ratio of the pixel output has a high value enabling the detection of a small defect.

As can be evident from the comparison with these comparison examples, the defect inspection tool 1 according to embodiments of the present invention and the imaging device 61 applied thereto enable inspections with high sensitivity and can improve the detection reproducibility of a defect.

Embodiments of the present invention are not limited to those stated above, which can be variously modified. For instance, the imaging device may include an imaging device made up of multiple sensor pixels arranged in a predetermined direction, and each sensor pixel has multiple sensor pixel borders defining an outer edge part of the sensor pixel, among which at least one of a pair of sensor pixel borders that are opposed in the arrangement direction may be oblique to the passage direction of the defect image that is vertical to the predetermined direction, and the specific shape thereof may be various shapes such as a trapezoidal shape.

The inspection tool is not limited for the inspection of the appearance of a semiconductor wafer. The processing and configuration of the detection signal processor 70 also can be modified suitably for the specific configuration of the imaging devices.

REFERENCE SIGNS LIST

1 Defect inspection tool
10 Light source
20, 20L, 20H Illumination optics
21 Illumination shaping optics
22 Beam expander
23 Polarizing device
25, 25L, 25H Irradiation optics
26, 26L, 26H Reflective mirror
27, 27L, 27H Collecting lens
30 Semiconductor wafer
31 Wafer surface
32 Illumination spot
40 Stage mechanism
41 Position detection encoder
50, 50L, 50H Imaging optics
51, 51L, 51H Detection lens
60, 60L, 60H Optical detector
61 Imaging device
63 Adder
70 Detection signal processor
71 A/D converter
72 Signal feature extraction unit
73 Defect information processing unit
74 Operation basic data storage unit
75 Symmetric judgment unit
76 Coordinates calculation unit
77 Neighboring image integration unit
78 Noise threshold storage unit
79 Adder
80 Control signal generator
ms Primary scanning direction
p Sensor pixel
q Sensor pixel border
df Defect image All publications, patents, and patent applications cited herein are incorporated herein by reference in their entirety.

The invention claimed is:

1. An inspection tool, comprising:
illumination optics configured to supply inspection light to a sample to define an illumination area on the sample;
an imaging device configured to detect light from the sample; and
a processor, wherein:
the imaging device includes multiple sensor pixels that are arranged in a direction substantially vertical to a main scanning direction of the illumination area on the sample,
a pair of sensor pixel borders opposed in the pixel arrangement direction are oblique to the main scanning direction, and
the processor is configured to:
determine whether a detection signal waveform from the multiple sensor pixels includes a peak, and
acquire a position of a defect on the sample based on a detection signal waveform determined to include a peak.

2. The inspection tool according to claim 1, wherein the processor acquires a position of the defect based on correlation of the detection signal waveform.

3. The inspection tool according to claim 2, wherein the processor acquires a position of the defect in the primary scanning direction based on a sampling rate and a sampling timing when the detection signal waveform is extracted.

4. The inspection tool according to claim 3, wherein the processor acquires a position of the defect in a secondary scanning direction based on a center position of a defect image when the detection signal waveform is obtained.

5. The inspection tool according to claim 4, wherein the processor acquires a variation of the correlation and changes the position of the defect in the secondary scanning direction based on the variation.

6. The inspection tool according to claim 5, further comprising a noise removal unit configured to remove a predetermined background noise component from an output signal of the sensor pixels and output the detection signal waveform.

7. The inspection tool according to claim 6, wherein the output signal has a sampling rate which is given by a predetermined driving signal that is shorter than a sampling time of the defect image.

8. The inspection tool according to claim 7, wherein the sensor pixels have a dimension that is substantially equal to an optical resolution of a defect to be detected.

9. The inspection tool according to claim 8, wherein each sensor pixel has a triangle shape.

10. The inspection tool according to claim 9, wherein each sensor pixel has an isosceles triangle shape.

11. The inspection tool according to claim 8, wherein each sensor pixel has a parallelogram shape.

12. The inspection tool according to claim 1, wherein the processor acquires a position of a defect in the primary scanning direction based on a sampling rate and a sampling timing when the detection signal waveform is extracted.

13. The inspection tool according to claim 1, wherein the processor acquires a position of a defect in a secondary scanning direction based on a center position of a defect image when the detection signal waveform is obtained.

14. The inspection tool according to claim 1, wherein the processor uses a variation of correlation of the detection signal waveform to change a position of a defect in a secondary scanning direction.

15. The inspection tool according to claim 1, further comprising a noise removal unit configured to remove a predetermined background noise component from an output signal of the sensor pixels and output the detection signal waveform.

16. The inspection tool according to claim 1, wherein an output signal of the sensor pixels has a sampling rate which is given by a predetermined driving signal that is shorter than a sampling time of a defect image.

17. The inspection tool according to claim 1, wherein the sensor pixels have a dimension that is substantially equal to an optical resolution of a defect to be detected.

18. The inspection tool according to claim 1, wherein each sensor pixel has a triangle shape.

19. The inspection tool according to claim 18, wherein each sensor pixel has an isosceles triangle shape.

20. The inspection tool according to claim 1, wherein each sensor pixel has a parallelogram shape.

\* \* \* \* \*

UNITED STATES PATENT AND TRADEMARK OFFICE
CERTIFICATE OF CORRECTION

PATENT NO.        : 9,791,380 B2
APPLICATION NO.   : 14/391338
DATED             : October 17, 2017
INVENTOR(S)       : Takahiro Jingu It is certified that error appears in the above-identified patent and that said Letters Patent is hereby corrected as shown below:

On the Title Page

Item (73) Assignee:
"HITACTHI HIGH-TECHNOLOGIES CORPORATION, Tokyo (JP)"
Should read:
--HITACHI HIGH-TECHNOLOGIES CORPORATION, Tokyo (JP)--.

Signed and Sealed this
Thirteenth Day of March, 2018

Andrei Iancu
*Director of the United States Patent and Trademark Office*